(12) United States Patent
Castro Palomino Laria et al.

(10) Patent No.: US 8,258,308 B2
(45) Date of Patent: Sep. 4, 2012

(54) AMINO NICOTINIC AND ISONICOTINIC ACID DERIVATIVES AS DHODH INHIBITORS

(75) Inventors: Julio Cesar Castro Palomino Laria, Barcelona (ES); Montserrat Erra Sola, Barcelona (ES); Maria Estrella Lozoya Toribio, Barcelona (ES); Eloisa Navarro Romero, Barcelona (ES)

(73) Assignee: Laboratorios Almirall, S.A., Barcelona (ES)

( * ) Notice: Subject to any disclaimer, the term of this patent is extended or adjusted under 35 U.S.C. 154(b) by 50 days.

(21) Appl. No.: 12/520,237

(22) PCT Filed: Dec. 21, 2007

(86) PCT No.: PCT/EP2007/011401
§ 371 (c)(1),
(2), (4) Date: Sep. 9, 2009

(87) PCT Pub. No.: WO2008/077639
PCT Pub. Date: Jul. 3, 2008

(65) Prior Publication Data
US 2010/0074898 A1    Mar. 25, 2010

(30) Foreign Application Priority Data

Dec. 22, 2006  (ES) .................................. 200603250
Apr. 23, 2007  (ES) .................................. 200701086

(51) Int. Cl.
C07D 211/78    (2006.01)
C07D 213/79    (2006.01)
C07D 421/00    (2006.01)
A61K 31/44     (2006.01)

(52) U.S. Cl. ..................... 546/318; 546/326; 546/268.1; 514/332

(58) Field of Classification Search .................. None
See application file for complete search history.

(56) References Cited

U.S. PATENT DOCUMENTS

| | | | |
|---|---|---|---|
| 5,780,592 A | 7/1998 | Müllner et al. | |
| 7,071,222 B2 | 7/2006 | Bartlett et al. | |
| 7,258,118 B2 | 8/2007 | Goede et al. | |
| 2003/0004171 A1 | 1/2003 | Humphrey et al. | |
| 2006/0081246 A1 | 4/2006 | Goede et al. | |
| 2011/0129445 A1 | 6/2011 | Godessart Marina et al. | |

FOREIGN PATENT DOCUMENTS

| | | |
|---|---|---|
| EP | 0 780 128 | 6/1997 |
| WO | WO 97/34600 | 1/1997 |
| WO | WO 97/00703 | 9/1997 |
| WO | WO 99/45926 | 9/1999 |
| WO | WO 00/76489 | 12/2000 |
| WO | WO 02/080897 | 10/2002 |
| WO | WO 03/000325 | 1/2003 |
| WO | WO 03/006425 | 1/2003 |
| WO | WO 03/061742 | 7/2003 |
| WO | WO 2004/048314 | 6/2004 |
| WO | WO 2004/056746 | 7/2004 |
| WO | WO 2004/056747 | 7/2004 |
| WO | WO 2005/075410 | 8/2005 |
| WO | WO 2006/001961 | 1/2006 |
| WO | WO 2006/022442 | 3/2006 |
| WO | WO 2006/044741 | 4/2006 |
| WO | WO 2006/122788 | 11/2006 |
| WO | WO 2008/097180 | 8/2008 |
| WO | WO 2009/021696 | 2/2009 |
| WO | WO 2009/153043 | 12/2009 |
| WO | WO 2010/083975 | 7/2010 |
| WO | WO 2010/102824 | 9/2010 |
| WO | WO 2010/102825 | 9/2010 |
| WO | WO 2010/102826 | 9/2010 |
| WO | WO 2011/045059 | 4/2011 |

OTHER PUBLICATIONS

Silverman, R. "The Organic Chemistry of Drug Design and Drug Action," 2004, Elsevier, pp. 29-32.*
HCAPLUS 1972:10360.*
Patani, G. et al., Chem. Rev. 1996, vol. 96, pp. 3147-3176.*
Silverman, R. "The Organic Chemistry of Drug Design and Drug Action," 2004, Elsevier, p. 9.*
U.S. Appl. No. 12/529,490, filed Feb. 9, 2010, Laria et al.
Baughman, RP et al. "Leflunomide for Chronic Sarcoidosis," *Clinical Research*, 21: 43-48 (2004).
Breedveld, FC et al. "Leflunomide: Mode of Action in the Treatment of Rheumatoid Arthritis," *Annals of the Rheumatic Diseases*, 59: 841-849 (2000).

(Continued)

*Primary Examiner* — Janet Andres
*Assistant Examiner* — Heidi Reese
(74) *Attorney, Agent, or Firm* — Finnegan, Henderson, Farabow, Garrett & Dunner, LLP

(57) ABSTRACT

The present disclosure relates to compounds of formula (I):

Formula (I):

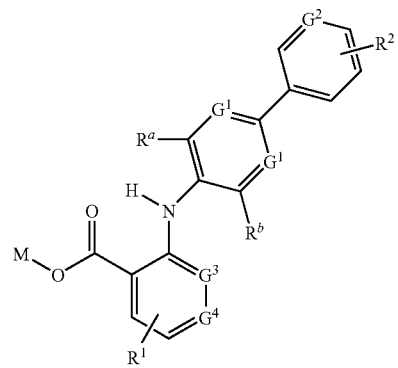

or a pharmaceutically acceptable salt or N-oxide thereof.
The present disclosure also relates to pharmaceutical compositions comprising the compounds of formula (I), and to their methods of use in therapy.

26 Claims, No Drawings

OTHER PUBLICATIONS

Dexter, DL et al. "Activity of a Novel 4-Quinolinecarboxylic Acid, NSC 368390 [6-Fluoro-2-(2'-fluoro-1,1'-biphenyl-4-yl)-3-methyl-4-quinolinecarboxylic Acid Sodium Salt], against Experimental Tumors," *Cancer Research*, 45: 5563-5568 (Nov. 1985).

Dimitrova, P. et al. "Restriction of De Novo Primidine Biosynthesis Inhibits Th1 Cell Activation and Promotes Th2 Cell Differentiation," *The Journal of Immunology*, 169:3392-3399 (2002).

Fox, RI "Mechanism of Action of Leflunomide in Rheumatoid Arthritis," *The Journal of Rheumatology*, 25, Supplement 53:20-26 (1998).

Haibel, J. et al. "Six Month Open Label Trial of Leflunomide in Active Ankylosing Spondylitis," *Annals of the Rheumatic Diseases*, 64: 124-126 (2005).

International Search Report mailed Oct. 20, 2008, for International Application No. PCT/EP2008/006573 (WO 2009/021696).

John, GT et al. "Leflunomide Therapy for Cytomegalovirus Disease in Renal Allograft Recipients," *Transplantation*, 77(9): 1460-1461 (2003).

Liu, S. et al. "Structures of Human Dihydroorotate Dehydrogenase in Complex with Antiproliferative Agents," *Structure*, 8(1): 25-33 (2000).

Löffler, M. et al. "Dihydroorotat-ubiquinone oxidoreductase links mitochondria in the biosynthesis of pyrimidine nucleotides," *Molecular and Cellular Biochemistry*, 174: 125-129 (1997).

Manna, SK et al. "Leflunomide Suppresses TNF-Induced Cellular Responses: Effects on NF-{kappa}B, Activator Protein-1, c-Jun N-Terminal Protein Kinase, and Apoptosis," *Journal of Immunology*, 165:5962-5969 (2000).

McRobert, L. et al. "RNA Interference (RNAi) Inhibits Growth of *Plasmodium falciparum*," *Molecular & Biochemical Parasitology*, 19: 273-278 (2002).

Metzler, C. et al. "Maintenance of Remission with Leflunomide in Wegener's Granulomatosis," *Rheumatology*, 43:315-320 (2004).

Miyaura, N. et al. "Palladium-Catalyzed Cross-Coupling Reactions of Organoboron Compounds," *Chemical Reviews*, 35:2457-2483 (1995).

O'Connor, PW et al. "A Phase II Study of the Safety and Efficacy of Teriflunomide in Multiple Sclerosis with Relapses," *Neurology*, 66:894-900 (2006).

Schläpfer, E. et al. "Anti-HIV-1 Activity of Leflunomide: a Comparison with Mycophenolic Acid and Hydroxyurea," *AIDS*, 17(11): 1613-1620 (2003).

Silverman, E. et al. "Long-Term Open-Label Preliminary Study of the Safety and Efficacy of Leflunomide in Patients with Polyarticular-Course Juvenile Rheumatoid Arthritis," *Arthritis & Rheumatism*, 52(2): 554-562 (2005).

Urushibara, M. et al. "The Antirheumatic Drug Leflunomide Inhibits Osteoclastogenesis by Interfering With Receptor Activator of NF-κB Ligand-Stimulated Induction of Nuclear Factor of Activated T Cells c1," *Arthritis & Rheumatism*, 50(3): 794-804 (2004).

English Language Derwent Abstract for WO 06/022442 (Mar. 2, 2006).

English Language Caplus Abstract for Spano, R. et al. "Preparation and pharmacology of some derivatives of 2-aminonicotinic," *Farmaco, Edizione Scientifica, Societa Chimica Italiana, Pavia, IT*, 26(9): 844-849 (1971).

Spano, R. et al. "Preparation and pharmacology of some derivatives of 2-aminonicotinic," *Farmaco, Edizione Scientifica, Societa Chimica Italiana, Pavia, IT*, 26(9): 844-849 (1971).

International Search Report mailed May 8, 2008, for International Application No. PCT/EP2007/011401 (WO 2008/077639 A1).

U.S. Appl. No. 13/256,104, filed Sep. 19, 2011, Garcia Gonzales et al.

U.S. Appl. No. 13/256,127, filed Sep. 19, 2011, Garcia Gonzales et al.

U.S. Appl. No. 13/256,349, filed Sep. 13, 2011, Perez Garcia et al.

Berge, S.M. et al., "Pharmaceutical Salts", Journal of Pharmaceutical Science, American Pharmaceutial Association, Washington, DC, vol. 66, No. 1, Jan. 1, 1977, pp. 1-19, XP00562636, ISSN: 0022-3549.

Gu, L. et al., "Preformulation Salt Selection. Physical Property Comparisons of the Tris (Hydroxymethyl) Aminomethane (THAM) Salts of Four Analgesic/Anti-inflammatory Agents with the Sodium Salts and the Free Acids," Pharmaceutical Research, Kluwer Academic Publishers, New York, NY, vol. 4, No. 3, Jan. 1, 1987, pp. 255-257, XP002099348, ISSN: 0724-8741.

International Search Report for International Application No. PCT/EP2010/001549 dated May 31, 2010.

International Search Report for International Application No. PCT/EP2010/001548 dated Nov. 18, 2010.

International Search Report for International Application No. PCT/EP2010/001550 mailed Apr. 23, 2010.

Stahl, P.H. et al., "Tromethamine", Handbook of Pharmaceutical Salts Properties, Selection and Use, Jan. 1, 2002, pp. 324-325, XP002214621.

U.S. Appl. No. 12/999,698, filed Dec. 17, 2010, Godessart Marina et al.

U.S. Appl. No. 13/145,628, filed Jul. 21, 2011, Godessart Marina et al.

ClinialTrials.gov Identifier: NCT00637819, Sanofi-Aventis, Double blind, randomized, placebo controlled pilot study of leflunomide in systemic lupus erythematosus (SLE) (2008).

International Search Report mailed Jul. 31, 2009, for International Application No. PCT/EP2009/004404 (WO 2009/153043).

International Search Report mailed Apr. 16, 2010, for International Application No. PCT/EP2010/000270 (WO 2010/083975).

Kremer, JM "Methotrexate and leflunomide: Biochemical basis for combination therapy in the treatment of rheumatoid arthritis," Seminars in Arthritis and Rheumatism, 29(1): 14-26 (1999).

Kremer, JM "Concomitant Leflunomide Therapy in Patients with Active Rheumatoid Arthritis despite Stable Doses of Methotrexate," Annals of Internal Medicine, 137(9): 726-733 (2002).

Kulkarni, OP et al. "4SC-101, A Novel Small Molecule Dihydroorotate Dehydrogenase Inhibitor, Suppresses Systemic Lupus Erythematosus in MRL-(Fas)lpr Mice," The American Journal of Pathology, 176(6): 2840-2847 (2010).

Leban, J. et al. "Biphenyl-4-ylcarbamoyl thiophene carboxylic acids as potent DHODH inhibitors," Bioorganic & Medicinal Chemistry Letters, 16(2): 267-270 (2006).

Majithia, V. et al. "Successful Treatment of Sarcoidosis with Leflunomide," Rheumatology, 42: 700-702 (2003).

Mehta, V. et al. "Leflunomide," Indian J. Dermatol. Venereol. Leprol., 75(4): 422-425 (2009).

Sanders, S. et al. "Leflunomide for the Treatment of Rheumatoid Arthritis and Autoimmunity," American Journal of the Medical Sciences, 323(4): 190-103(2002).

Tlacuilo Parra, JA et al. "Leflunomide in the treatment of psoriasis: results of a phase II open trial," British Journal of Dermatology, 150: 970-976 (2004).

Weinblatt, ME et al. "Pharmacokinetics, safety, and efficacy of combination treatment with methotrexate and leflunomide in patients with active rheumatoid arthritis," Arthritis & Rheumatism, 42(7): 1322-1328 (Jul. 1999).

U.S. Appl. No. 13/501,847, filed Apr. 13, 2012, Boix Bernardini.

International Search Report for International Application No. PCT/EP2010/006283 (WO 2011/045059) datedNov. 12, 2010.

Batt, Douglas G., "Inhibitors of dihydroorotate dehydrogenase," Expert Opinion on Therapeutic Patents, 9(1):41-54 (1999).

Vyas, V. K. et al., "Recent developments in the medicinal chemistry and therapeutic potential of dihydroorotate dehydrogenase (DHODH) inhibitors," Mini-Reviews in Medicinal Chemistry, 11:1039-1055 (2011).

Phillips, Margaret A., et al., "Triazolopyrimidinc-based dihydroorotate dehydrogenase inhibitors with potent and selective activity against the malaria parasite *Plasmodium falciparum*," J. Med. Chem., 51:3649-3653 (2008).

\* cited by examiner

AMINO NICOTINIC AND ISONICOTINIC ACID DERIVATIVES AS DHODH INHIBITORS

This application is a national stage filing under 35 U.S.C. §371 of International Application No. PCT/EP2007/011401 filed on 21 Dec. 2007, which claims priority of Spanish Patent Application No. P200701086, filed on 23 Apr. 2007 and Spanish Patent Application No. P200603250, filed on 22 Dec. 2006. The contents of all three applications are incorporated herein by reference.

The present invention relates to new inhibitors of the dehydroorotate dihydrogenase (DHODH). These compounds are useful in the treatment, prevention or suppression of diseases and disorders known to be susceptible to improvement by inhibition of dihydroorotate dehydrogenase, such as autoimmune diseases, immune and inflammatory diseases, destructive bone disorders, malignant neoplastic diseases, angiogenic-related disorders, viral diseases, and infectious diseases.

The enzyme dihydroorotate dehydrogenase (DHODH) is the enzyme that catalyzes the fourth step in the pyrimidine biosynthetic pathway namely the conversion of dihydroorotate to orotate concomitantly with a electron transfer to ubiquinone (cofactor Q) via a flavin mononucleotide intermediate (Leffler et al Mol Cell Biochem, 1997). In contrast to parasites (*Plasmodium falciparum*) (McRobert et al Mol Biochem Parasitol 2002) and bacteria (*E. coli*) which exclusively have this de novo pathway as the source of pyrimidines, mammal cells have an additional salvage pathway.

During homeostatic proliferation, the salvage pathway which is independent of DHODH seems sufficient for the cellular supply with pyrimidine bases. Only, cells with a high turnover and particularly T and B lymphocytes need the de novo pathway to proliferate. In these cells, DHODH inhibition stops the cell cycle progression suppressing DNA synthesis and consequently cell proliferation (Breedveld F C et al Ann Rheum Dis 2000). Therefore, inhibitors of DHODH show beneficial immunosuppressant and antiproliferative effects in human diseases characterized by abnormal and uncontrollable cell proliferation causing chronic inflammation and tissue destruction.

In addition to abolish lymphocyte proliferation inhibitors of DHODH (i.e. teriflunomide, Maritimus (FK778) and brequinar) have an anti-inflammatory action by inhibition of cytokine production and nuclear factor (NF)-kB-signalling, monocyte migration and increased production of transforming growth factor beta-1 and induces a shift from T helper cell type 1 (Th1) to type 2 (Th2) subpopulation differentiation (Manna et al. J Immunol 2000)(Dimitrova et al J. Immunol. 2002). Furthermore, the osteoclast differentiation mediated by RANKL decreased by DHODH inhibition (Urushibara et al. Arthrititis Rheum 2004)

In co-crystallisation experiments with two inhibitors of DHODH that reached clinical trials, Brequinar (Dexter D. L. et al.; Cancer Res. 1985) and Teriflunomide (A77-1726), were both found to bind in a common site, that is also believed to be the binding site of the cofactor ubiquinone (Liu et al; Struc. Fold. Des. 2000).

Leflunomide sold under the trade name Arava (EP 0 780 128, WO 97/34600), was the first DHODH inhibitor that reached the market place. Leflunomide is the prodrug of teriflunomide, which is the active metabolite inhibiting human DHODH with a moderate potency (Fox et al, J. Rheumatol. Suppl. 1998).

Leflunomide is a DMARD (disease modifying anti-rheumatic drug) from Aventis, which was approved by the FDA for the treatment of rheumatoid arthritis in 1998 and by the EMEA for the treatment of psoriatic arthritis in 2004. Currently Leflunomide is under active development for the treatment of systemic lupus erythematosus, Wegener's granulomatosis (Metzler et al; Rheumatology 2004; 43(3), 315-320) and HIV infection. Moreover, teriflunomide, its active metabolite is efficacious in multiple sclerosis and right now is in Phase III clinical trials (O'Connor et al Neurology 2006).

Other data are emerging in other closely related diseases such as ankylosing spondilitis (Haibel et al.; Ann. Rheum. Dis. 2005), polyarticular juvenile idiopathic arthritis (Silverman et al.; Arthritis Rheum. 2005) and Sarcoidosis (Baughman et al.; Sarcoidosis Vasc. Diffuse Lung Dis. 2004). Furthermore, leflunomide and FK778 have shown and excellent antiviral activity against cytomegalovirus. Leflunomide is currently indicated as second-line therapy for cytomegalovirus disease after organ transplantation (John et al Transplantation 2004). In addition Leflunomide reduces HIV replication by about 75% at concentration that can be obtained with conventional dosing (Schlapfer E et al. AIDS 2003)

In view of the physiological effects mediated by inhibition of dehydroorotate dehydrogenase, several DHODH inhibitors have been recently disclosed for the treatment or prevention of autoimmune diseases, immune and inflammatory diseases, destructive bone disorders, malignant neoplastic diseases, angiogenic-related disorders, viral diseases, and infectious diseases. See for example WO 06/044741; WO 06/022442; WO 06/001961, WO 04/056747, WO 04/056746, WO 03/006425, WO 02/080897 and WO 99/45926.

Diseases or disorders in which DHODH inhibition plays a role include without limitation autoimmune diseases, immune and inflammatory diseases, destructive bone disorders, malignant neoplastic diseases, angiogenic-related disorders, viral diseases, and infectious diseases.

Autoimmune diseases which may be prevented or treated include but are not limited to rheumatoid arthritis, psoriatic arthritis, systemic lupus erythematosus, multiple sclerosis, psoriasis, ankylosing spondilytis, Wegener's granulomatosis, polyarticular juvenile idiopathic arthritis, inflammatory bowel disease such as ulcerative colitis and Crohn's disease, Reiter's syndrome, fibromyalgia and type-1 diabetes.

Immune and inflammatory diseases which may be prevented or treated include but are not limited to asthma, COPD, respiratory distress syndrome, acute or chronic pancreatitis, graft versus-host disease, chronic sarcoidosis, transplant rejection, contact dermatitis, atopic dermatitis, allergic rhinitis, allergic conjunctivitis, Behcet syndrome, inflammatory eye conditions such as conjunctivitis and uveitis.

Destructive bone disorders which may be prevented or treated include but are not limited to osteoporosis, osteoarthritis and multiple myeloma-related bone disorder.

Malignant neoplastic diseases that may be prevented or treated include but are not limited to prostate, ovarian and brain cancer.

Agiogenesis-related disorders that may be prevented or treated include but are not limited to hemangiomas, ocular neovascularization, macular degeneration or diabetic retinopathy.

Viral diseases which may be prevented or treated include but are not limited to HIV infection, hepatitis and cytomegalovirus infection.

Infectious diseases which may be prevented or treated include but are not limited to sepsis, septic shock, endotoxic shock, Gram negative sepsis, toxic shock syndrome, Shigellosis and other protozoal infestations such as malaria.

It has now been found that certain amino(iso)nicotinic acid derivatives are novel potent inhibitors of DHODH and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible to improvement by inhibition of DHODH wherein the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis and methods of treatment of pathological conditions or diseases susceptible to amelioration by inhibition of DHODH wherein the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis comprising the administration of the compounds of the invention to a subject in need of treatment.

Thus, the present invention is directed to new amino(iso) nicotinic acid derivatives of formula (I)

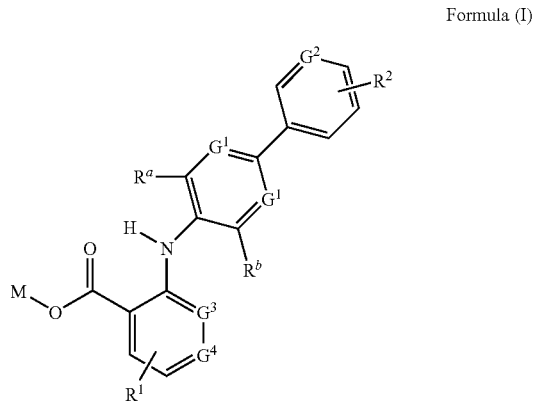

Formula (I)

wherein:
one of the groups $G^1$ represents a nitrogen atom or a group $CR^c$ and the other represents a group $CR^c$
$G^2$ represents a nitrogen atom or a group $CR^d$
$R^1$ represents a group selected from hydrogen atoms, halogen atoms, $C_{1-4}$ alkyl groups which may be optionally substituted by 1, 2 or 3 substituents selected from halogen atoms and hydroxy groups, and $C_{3-8}$ cycloalkyl groups which may be optionally substituted by 1, 2 or 3 substituents selected from halogen atoms and hydroxy groups
$R^2$ represents a group selected from hydrogen atoms, halogen atoms, hydroxyl groups, $C_{1-4}$ alkyl groups which may be optionally substituted by 1, 2 or 3 substituents selected from halogen atoms and hydroxy groups, $C_{1-4}$ alkoxy groups which may be optionally substituted by 1, 2 or 3 substituents selected from halogen atoms and hydroxy groups, and $C_{3-8}$ cycloalkyl groups which may be optionally substituted by 1, 2 or 3 substituents selected from halogen atoms and hydroxy groups
$R^a$, $R^b$ and $R^c$ independently represent groups selected from hydrogen atoms, halogen atoms, $C_{1-4}$ alkyl groups which may be optionally substituted by 1, 2 or 3 substituents selected from halogen atoms and hydroxy groups, and $C_{1-4}$ alkoxy groups which may be optionally substituted by 1, 2 or 3 substituents selected from halogen atoms and hydroxy groups
$R^d$ represents a group selected from hydrogen atoms, halogen atoms, hydroxyl groups, $C_{1-4}$ alkyl groups which may be optionally substituted by 1, 2 or 3 substituents selected from halogen atoms and hydroxy groups, and $C_{1-4}$ alkoxy groups which may be optionally substituted by 1, 2 or 3 substituents selected from halogen atoms and hydroxy groups, and $C_{3-8}$ cycloalkoxy groups which may be optionally substituted by 1, 2 or 3 substituents selected from halogen atoms and hydroxy groups
one of the groups $G^3$ and $G^4$ is a nitrogen atom and the other is a CH group,
M is a hydrogen atom or an pharmaceutically acceptable cation
with the proviso that, when at least one of the groups $R^a$ and $R^b$ represent a hydrogen atom and $G^2$ is a group $CR^d$, then $R^d$ represents a group selected from $C_{1-4}$ alkoxy groups which may be optionally substituted by 1, 2 or 3 substituents selected from halogen atoms and hydroxy groups, $C_{3-8}$ cycloalkoxy groups which may be optionally substituted by 1, 2 or 3 substituents selected from halogen atoms and hydroxy groups;
and the pharmaceutically acceptable salts and N-oxides thereof.

As used herein the term alkyl embraces optionally substituted, linear or branched hydrocarbon radicals having 1 to 4 carbon atoms. Preferred substituents on the alkyl groups are halogen atoms and hydroxy groups, and are more preferably halogen atoms.

Examples include methyl, ethyl, n-propyl, i-propyl, n-butyl, sec-butyl and tert-butyl radicals.

As used herein the term alkoxy embraces optionally substituted, linear or branched oxy-containing radicals each having 1 to 4 carbon atoms. Preferred substituents on the alkoxy groups are halogen atoms and hydroxy groups, and are more preferably halogen atoms.

Examples include methoxy, ethoxy, n-propoxy, i-propoxy, n-butoxy, sec-butoxy and tert-butoxy radicals.

As used herein, the term cycloalkyl embraces saturated carbocyclic radicals and, unless otherwise specified, a cycloalkyl radical typically has from 3 to 8 carbon atoms.

Examples include cyclopropyl, cyclobutyl, cyclopentyl, cyclohexyl and cycloheptyl. When a cycloalkyl radical carries 2 or more substituents, the substituents may be the same or different. Preferred substituents on the cycloalkyl groups are halogen atoms and hydroxy groups, and are more preferably halogen atoms.

As used herein, the term cycloalkoxy embraces saturated oxy-containing carbocyclic radicals and, unless otherwise specified, a cycloalkoxy radical typically has from 3 to 8 carbon atoms.

Examples include cyclopropyloxy, cyclobutyloxy, cyclopentyloxy, cyclohexyloxy and cycloheptyloxy. When a cycloalkoxy radical carries 2 or more substituents, the substituents may be the same or different. Preferred substituents on the cycloalkoxy groups are halogen atoms and hydroxy groups, and are more preferably halogen atoms.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

As used herein, the term halogen atom embraces chlorine, fluorine, bromine or iodine atoms typically a fluorine, chlorine or bromine atom, most preferably bromine or fluorine. The term halo when used as a prefix has the same meaning.

M may be a hydrogen atom or a pharmaceutically acceptable cation. When M is a pharmaceutically acceptable cation, the compound represented by formula (I) may alternatively be represented by formula (I*) below.

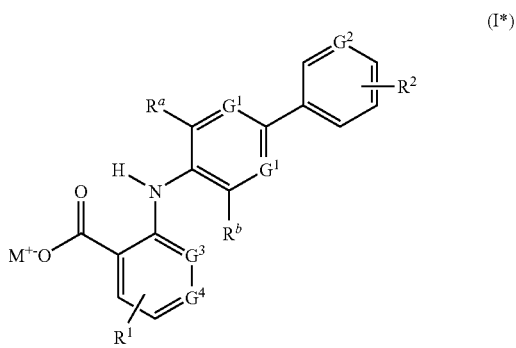

(I*)

As used herein, the term pharmaceutically acceptable cation embraces both inorganic cations, for example alkali metal cations ($Li^+$, $Na^+$, $K^+$), alkaline earth cations ($Ca^{2+}$, $Mg^{2+}$) and other pharmaceutically acceptable inorganic cations known in the art ($Zn^{2+}$, $Al^{3+}$), and organic cations, for example ammonium ion (i.e., $NH_4^+$) and substituted ammonium ions, such as $NH_3R^{1+}$, $NH_2(R^1)_2^+$, $NH(R^1)_3^+$ and N$(R^1)_4^+$, where each $R^1$ is independently selected from a phenyl group, a benzyl group, $C_{1-4}$ alkyl and $C_{3-8}$ cycloalkyl.

Examples of some suitable substituted ammonium ions are $EtNH_3^+$, $Et_2NH_2^+$, $Et_3NH^+$, $(C_6H_{11})_2NH_2^+$, $CH_3CH_2CH_2CH_2NH_3^+$, $PhCH_2NH_3^+$ and $(Ph)(PhCH_2)NH_2^+$. An example of a common quaternary ammonium ion is $N(CH_3)_4^+$.

Typically, M is a hydrogen atom or a pharmaceutically acceptable cation selected from $Li^+$, $Na^+$, $K^+$, $Ca^{2+}$ and $Mg^{2+}$. It is preferred that M is a hydrogen atom or a pharmaceutically acceptable cation selected from $Li^+$, $Na^+$ and $K^+$. More preferably M is a hydrogen atom or $Li^+$, and most preferred is when M is a hydrogen atom.

If M of formula (I) is a pharmaceutically acceptable cation having a charge greater than +1, then additional anions are present to maintain the electroneutrality of the compound. The counteranion may be an anion X— as defined below or an anion as represented in formula (I*) above.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic, cyclohexylsulfamic (cyclamic) or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

As used herein, an N-oxide is formed from the tertiary basic amines or imines present in the molecule, using a convenient oxidising agent.

In an embodiment of the present invention $R^1$ is selected from the group consisting of hydrogen, bromine and fluorine atoms, methyl, ethyl, cyclopropyl and cyclobutyl.

In another embodiment of the present invention $G^3$ represents a nitrogen atom and $G^4$ represents a group CH.

In still another embodiment of the present invention $G^3$ represents a group CH and $G^4$ represents a nitrogen atom.

In yet another embodiment of the present invention both groups $G^1$ represent a group $CR^c$.

In another embodiment of the present invention each $R^c$ is independently selected from the groups consisting of hydrogen atoms, fluorine atoms, chlorine atoms and $C_{1-3}$ alkyl groups.

In still another embodiment of the present invention the group $G^2$ represents a group $CR^d$.

In yet another embodiment of the present invention $R^d$ is selected from the groups consisting of hydroxy, $C_{1-3}$ alkoxy groups, 2,2,2-trifluoroethoxy and $C_{3-4}$cycloalkoxy groups. Preferably, $C_{1-3}$ alkoxy groups, 2,2,2-trifluoroethoxy and $C_{3-4}$cycloalkoxy groups.

In another embodiment of the present invention $R^a$ is selected from the groups consisting of fluorine atoms, methyl groups and trifluoromethoxy groups.

In still another embodiment of the present invention $R^b$ is selected from the group consisting of hydrogen atoms, fluorine atoms and chlorine atoms.

In yet another embodiment of the present invention $R^2$ is selected from the group consisting of hydrogen atoms and halogen atoms, preferably hydrogen atoms and fluorine atoms.

In a preferred embodiment of the present invention both groups $G^1$ represent $C(R^c)$ groups, $G^2$ represents a $C(R^d)$ group, preferably $G^2$ is a group selected from C(OH), C(OMe) and C(OEt); $R^a$ is a fluorine atom, $R^b$ is selected from the group consisting of hydrogen atoms and fluorine atoms and $R^1$ is selected from the group consisting of hydrogen, bromine and fluorine atoms, methyl, ethyl and cyclopropyl groups, Preferably, both $G^1$ represent CH groups, $G^2$ is a group selected from C(OMe) and C(OEt); $R^a$ is a fluorine atom, $R^b$ is selected from the group consisting of hydrogen atoms and fluorine atoms and $R^1$ is selected from the group consisting of hydrogen, bromine and fluorine atoms, methyl, ethyl and cyclopropyl groups.

In a preferred embodiment of the present invention, Fr is a hydrogen atom, $R^d$ is a hydroxy or a $C_{1-3}$ alkoxy groups and $R^2$ is a hydrogen atom, preferably $R^c$ is a hydrogen atom, $R^d$ is a $C_{1-3}$ alkoxy and $R^2$ is a hydrogen atom.

Particularly preferred are the compounds wherein $G^3$ represents a nitrogen atom, $G^4$ represents a group CH and $R^b$ is a fluorine atom and the compounds wherein $G^3$ represents a group CH, $G^4$ represents a nitrogen atom.

In a preferred embodiment of the present invention both groups $G^1$ represent $C(R^c)$ groups, $G^2$ represents $C(R^d)$ group, $R^a$ is a fluorine atom, $R^b$ is selected from the group consisting of hydrogen atoms and fluorine atoms and $R^1$ is selected from the group consisting of hydrogen, bromine and fluorine atoms, methyl, ethyl and cyclopropyl groups, Preferably $R^c$ is a hydrogen atom, $R^d$ is selected from the group consisting of $C_{1-3}$ alkoxy and $C_{3-4}$ cycloalkoxy groups and $R^2$ is a hydrogen atom. Particularly preferred are the compounds wherein $G^3$ represents a nitrogen atom, $G^4$ represents a group CH and $R^b$ is a fluorine atom and the compounds wherein $G^3$ represents a group CH, $G^4$ represents a nitrogen atom.

Particular individual compounds of the invention include:
2-(3-Fluoro-3'-methoxybiphenyl-4-ylamino)nicotinic acid
2-(3'-Ethoxy-3-fluorobiphenyl-4-ylamino)nicotinic acid
2-(3-Fluoro-3'-(trifluoromethoxy)biphenyl-4-ylamino)nicotinic acid
2-(3'-Ethoxy-3-(trifluoromethoxy)biphenyl-4-ylamino)nicotinic acid
2-(3'-Methoxy-3-(trifluoromethoxy)biphenyl-4-ylamino)nicotinic acid
2-(2,5-Difluoro-3'-methoxybiphenyl-4-ylamino)nicotinic acid
2-(3'-Ethoxy-2,5-difluorobiphenyl-4-ylamino)nicotinic acid
2-(2',3-difluoro-3'-methoxybiphenyl-4-ylamino)nicotinic acid
2-(2-Methyl-3'-(trifluoromethoxy)biphenyl-4-ylamino)nicotinic acid
2-(3-Chloro-3'-(trifluoromethoxy)biphenyl-4-ylamino)nicotinic acid
2-(3-Chloro-3'-ethoxybiphenyl-4-ylamino)nicotinic acid
2-(3-Methyl-3'-(trifluoromethoxy)biphenyl-4-ylamino)nicotinic acid
2-(3-Chloro-3'-methoxybiphenyl-4-ylamino)nicotinic acid
2-(3'-(Difluoromethoxy)-3-fluorobiphenyl-4-ylamino)nicotinic acid
2-(3'-Cyclobutoxy-3-fluorobiphenyl-4-ylamino)nicotinic acid
2-(3-Fluoro-3'-(2,2,2-trifluoroethoxy)biphenyl-4-ylamino)nicotinic acid
2-(3'-Cyclobutoxy-3,5-difluorobiphenyl-4-ylamino)nicotinic acid
2-(3,5-Difluoro-3'-(trifluoromethoxy)biphenyl-4-ylamino)nicotinic acid
2-(3'-Ethoxy-3,5-difluorobiphenyl-4-ylamino)nicotinic acid
2-(3,5-Difluoro-3'-methoxybiphenyl-4-ylamino)nicotinic acid
Lithium 3-(3'-ethoxy-3-fluorobiphenyl-4-ylamino)isonicotinate
Lithium 3-(3-fluoro-3'-methoxybiphenyl-4-ylamino)isonicotinate
Lithium 3-(3'-methoxy-3-(trifluoromethoxy)biphenyl-4-ylamino)isonicotinate
Lithium 3-(3-fluoro-3'-(trifluoromethoxy)biphenyl-4-ylamino)isonicotinate
2-(3'-Ethoxybiphenyl-4-ylamino)nicotinic acid
2-(5-Fluoro-2-methyl-3'-(trifluoromethoxy)biphenyl-4-ylamino)nicotinic acid
2-(2',3-Difluoro-5'-isopropoxybiphenyl-4-ylamino)nicotinic acid
2-(3-Fluoro-3'-methoxybiphenyl-4-ylamino)-5-methylnicotinic acid
2-(3,5-Difluoro-3'-hydroxybiphenyl-4-ylamino)nicotinic acid
5-Bromo-2-(3-fluoro-3'-methoxybiphenyl-4-ylamino)nicotinic acid
5-Bromo-2-(3,5-difluoro-3'-methoxybiphenyl-4-ylamino)nicotinic acid
5-Bromo-2-(3-fluoro-3'-(trifluoromethoxy)biphenyl-4-ylamino)nicotinic acid
2-(3-Fluoro-3'-(trifluoromethoxy)biphenyl-4-ylamino)-5-methylnicotinic acid
5-Cyclopropyl-2-(3-fluoro-3'-methoxybiphenyl-4-ylamino)nicotinic acid
2-(3,5-Difluoro-3'-methoxybiphenyl-4-ylamino)-5-methylnicotinic acid
2-(3'-Ethoxy-5-fluoro-2-methylbiphenyl-4-ylamino)nicotinic acid
2-(5-Fluoro-3'-methoxy-2-methylbiphenyl-4-ylamino)nicotinic acid
2-(3'-ethoxy-3,5-difluorobiphenyl-4-ylamino)-5-methylnicotinic acid
5-cyclopropyl-2-(3'-ethoxy-3,5-difluorobiphenyl-4-ylamino)nicotinic acid
2-(3,5-difluoro-3'-methoxybiphenyl-4-ylamino)-5-ethylnicotinic acid
5-bromo-2-(3'-ethoxy-2,5-difluorobiphenyl-4-ylamino)nicotinic acid
5-cyclopropyl-2-(3'-ethoxy-2,5-difluorobiphenyl-4-ylamino)nicotinic acid
2-(5-fluoro-3'-methoxy-2-methylbiphenyl-4-ylamino)-5-methylnicotinic acid
5-cyclopropyl-2-(5-fluoro-3'-methoxy-2-methylbiphenyl-4-ylamino)nicotinic acid
2-(2',3,5-trifluoro-3'-methoxybiphenyl-4-ylamino)nicotinic acid
2-(2'-chloro-3,5-difluorobiphenyl-4-ylamino)nicotinic acid
2-(3'-cyclopropoxy-3,5-difluorobiphenyl-4-ylamino)nicotinic acid
2-(3,5-difluoro-2-methylbiphenyl-4-ylamino)nicotinic acid
5-cyclopropyl-2-(2,5-difluoro-3'-methoxybiphenyl-4-ylamino)nicotinic acid
2-(3'-cyclopropoxy-3,5-difluorobiphenyl-4-ylamino)-5-cyclopropylnicotinic acid
5-chloro-2-(3,5-difluoro-3'-methoxybiphenyl-4-ylamino)nicotinic acid
5-cyclopropyl-2-(3,5-difluoro-3'-(trifluoromethoxy)biphenyl-4-ylamino)nicotinic acid
2-(2,3,5-trifluoro-3'-methoxybiphenyl-4-ylamino)nicotinic acid
2-(2'-chloro-3,5-difluorobiphenyl-4-ylamino)-5-cyclopropylnicotinic acid
2-(3,5-difluoro-3'-methoxy-2-methylbiphenyl-4-ylamino)nicotinic acid
2-(3,5-difluoro-2-methyl-3'-(trifluoromethoxy)biphenyl-4-ylamino)nicotinic acid
2-(2'-chloro-3,5-difluoro-2-methylbiphenyl-4-ylamino)nicotinic acid
5-chloro-2-(3,5-difluorobiphenyl-4-ylamino)nicotinic acid
5-chloro-2-(2'-chloro-3,5-difluorobiphenyl-4-ylamino)nicotinic acid
2-(2,3,5,6-tetrafluoro-3'-methoxybiphenyl-4-ylamino)nicotinic acid
2-(3,5-difluoro-2'-methylbiphenyl-4-ylamino)nicotinic acid
3-(3'-cyclopropoxy-3-fluorobiphenyl-4-ylamino)isonicotinic acid
Of outstanding interest are:
2-(3'-Ethoxy-3-(trifluoromethoxy)biphenyl-4-ylamino)nicotinic acid
2-(3'-Methoxy-3-(trifluoromethoxy)biphenyl-4-ylamino)nicotinic acid
2-(3'-Ethoxy-3,5-difluorobiphenyl-4-ylamino)nicotinic acid
2-(3,5-Difluoro-3'-methoxybiphenyl-4-ylamino)nicotinic acid
Lithium 3-(3'-ethoxy-3-fluorobiphenyl-4-ylamino)isonicotinate
Lithium 3-(3-fluoro-3'-methoxybiphenyl-4-ylamino)isonicotinate Lithium 3-(3'-methoxy-3-(trifluoromethoxy)biphenyl-4-ylamino)isonicotinate
2-(3-Fluoro-3'-methoxybiphenyl-4-ylamino)-5-methylnicotinic acid
5-Bromo-2-(3,5-difluoro-3'-methoxybiphenyl-4-ylamino)nicotinic acid
5-Cyclopropyl-2-(3-fluoro-3'-methoxybiphenyl-4-ylamino)nicotinic acid
2-(3,5-Difluoro-3'-methoxybiphenyl-4-ylamino)-5-methylnicotinic acid
2-(3,5-difluoro-3'-methoxybiphenyl-4-ylamino)-5-ethylnicotinic acid
2-(2'-chloro-3,5-difluorobiphenyl-4-ylamino)nicotinic acid
2-(3'-cyclopropoxy-3,5-difluorobiphenyl-4-ylamino)nicotinic acid
2-(3,5-difluoro-2-methylbiphenyl-4-ylamino)nicotinic acid
5-cyclopropyl-2-(2,5-difluoro-3'-methoxybiphenyl-4-ylamino)nicotinic acid
5-cyclopropyl-2-(3,5-difluoro-3'-(trifluoromethoxy)biphenyl-4-ylamino)nicotinic acid
2-(2'-chloro-3,5-difluorobiphenyl-4-ylamino)-5-cyclopropylnicotinic acid
2-(2,3,5,6-tetrafluoro-3'-methoxybiphenyl-4-ylamino)nicotinic acid Compounds of general formula (I) may be prepared following the synthetic scheme depicted in FIG. 1.

The compounds of general formula (Ia) (nicotinic acid derivatives) may be prepared by the reaction of these intermediates (II) with the corresponding chloronicotinic acid (III) in acid media such as acetic acid as a solvent or acetic acid or p-toluenesulphonic acid with a high boiling point solvent such as water, xylene, ethoxyethanol, DME or DMF at a temperature from 100 to 160° C. These compounds can also be prepared in basic media such as DBU, DIEA or $Cs_2CO_3$ in a high boiling point solvent such as xylene, ethoxyethanol, DMF or NMP.

The compounds of general formula (Ib) (isonicotinic acid derivatives) may be prepared by the saponification of the corresponding methyl ester (V) with a base such as lithium hydroxide or sodium hydroxide using a solvent miscible with water such as ethanol or methanol at a temperature from 0 to 50° C. yielding the corresponding salt.

Compounds of formula (V) may be obtained by coupling the biarylanilines (II) with the corresponding methyl chloroisonicotinate (IV). These reactions may be catalyzed by a palladium catalyst such as tris(dibenzylideneacetone)-dipalladium(0), with a ligand such as 9,9-dimethyl-4,5-bis(diphenylphosphino)-9H-xanthene and in the presence of an inorganic base such as cesium carbonate in an inert solvent such as toluene, dioxane or dimethylformamide, at a temperature from 80° C. to the boiling point of the solvent.

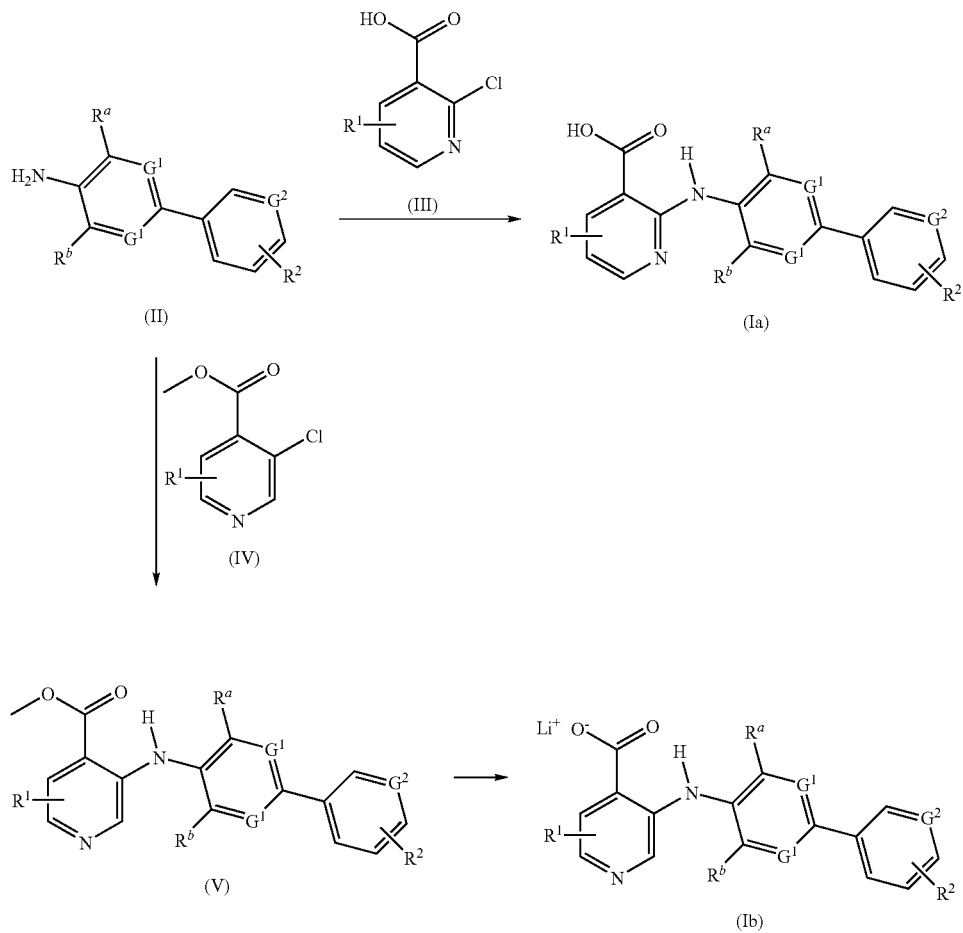

FIG. 1

The biaryanilines of formula (II) may be prepared following the synthetic scheme depicted in FIG. 2.

FIG. 2

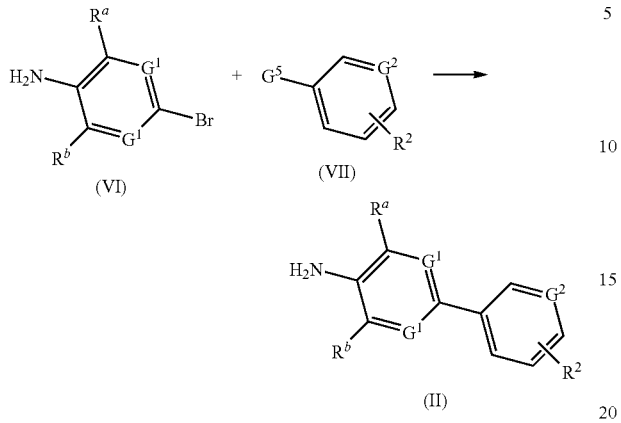

(II)

A bromoderivative of formula (VI) is coupled with the corresponding aryl derivative of formula (VII) under the conditions of a Suzuki reaction (Miyaura, N.; Suzuki, A. Chem. Rev. 1995, 95, 2457) wherein $G^5$ represents boronic acids or boronates or under the conditions of a Stille reaction wherein $G^5$ represents stannanes. These reactions may be catalyzed by a palladium catalyst such as [1,1'-bis(diphenylphosphino)-ferrocene]dichloropalladium (II) complex with dichloromethane (1:1), tetrakis(triphenylphosphine)-palladium(0), bis(triphenylphosphine)palladium(II) chloride or tris(dibenzylideneacetone)-dipalladium(0) in an aprotic organic solvent such as dioxane, toluene, DMF or DME and in the presence of a base such as cesium carbonate, sodium carbonate, potassium carbonate or potassium phosphate at a temperature from 80° C. to 140° C.

In the particular case where $R^a$ and $R^b$ are both different from hydrogen, the compounds of formula (Ia) may be obtained following the synthetic path shown in FIG. 3.

FIG. 3

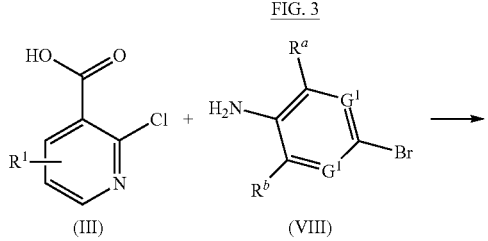

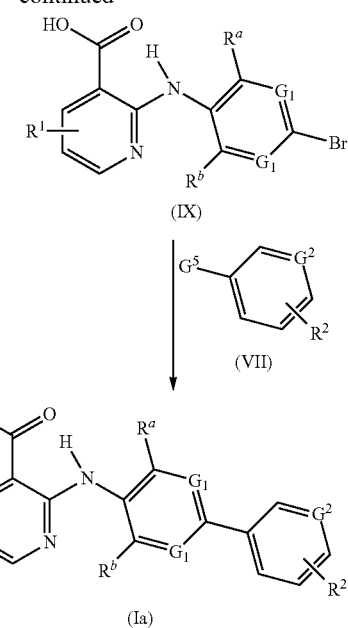

The compounds of formula (Ia) may be obtained from 2-(4-bromophenylamino)nicotinic acids of formula (IX) and the corresponding aryl derivative of formula (VII) under the conditions of a Suzuki reaction (Miyaura, N.; Suzuki, A. Chem. Rev. 1995, 95, 2457) wherein $G^5$ represents boronic acids or boronates or under the conditions of a Stille reaction wherein $G^5$ represents stannanes.

The 2-(4-bromophenylamino)nicotinic acids of formula (IX) may be obtained by the reaction of the bromoanilines of formula (VIII) with the corresponding chloronicotinic acid (III) in acid media such as acetic acid as a solvent or with a high boiling point solvent such as xylene, ethoxyethanol or DMF at a temperature from 100 to 160° C. Alternatively, the reaction can be carried out in basic media such as DBU, DIEA or $Cs_2CO_3$ in a high boiling point solvent such as xylene, ethoxyethanol, DMF or NMP.

In the particular case where $G^2$ is $CR^d$ and $R^d$ is hydroxyl the compounds of formula (Ia2) may be prepared following the synthetic path shown in FIG. 4.

FIG. 4

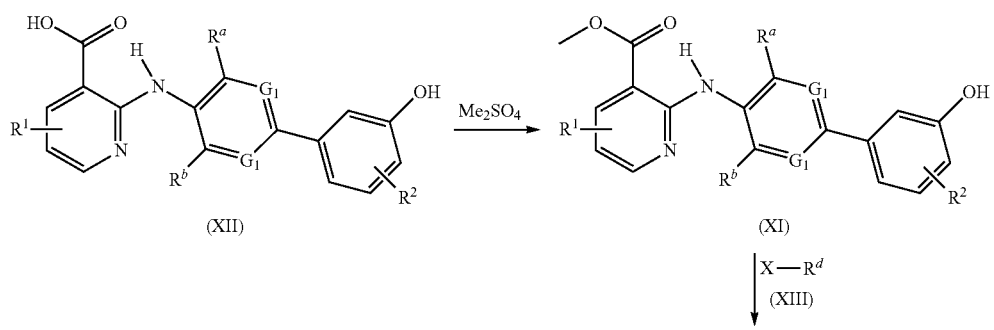

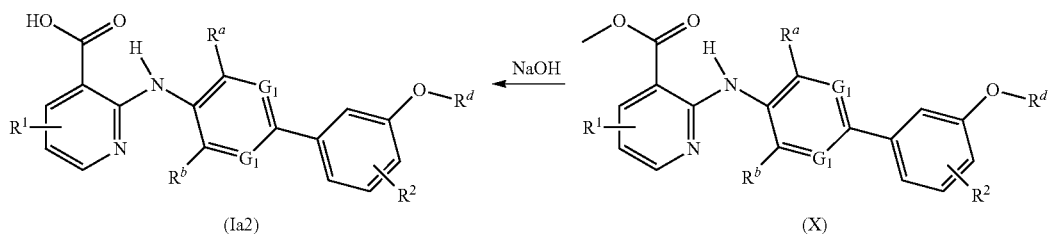

(Ia2) ← NaOH ← (X)

The reaction of the nicotinic acid of formula (XII) with a methylating reagent such as dimethyl sulphate, with an inorganic base such as sodium hydrogen carbonate in a solvent such as acetone at a temperature from 0 to the boiling point of the solvent, yield the methyl nicotinate compounds of formula (XI).

Reaction of methyl nicotinate of formula (XI) with an alkylating agent of formula (XIII), wherein $R^d$ is as hereinbefore defined and X is a leaving group such as chlorine or a bromine atom by standard methods yields the compounds of formula (X).

Finally, hydrolysis of the methyl nicotinate of formula (X) with a base such as lithium hydroxide or sodium hydroxide in a protic solvent such as methanol or ethanol at a temperature from 0 to 50° C., yield the desired compounds of formula (Ia2).

In the particular case where $R^1$ is $C_{1-4}$ alkyl groups or $C_{3-8}$ cycloalkyl groups the compounds of formula (Ia3) may be prepared following the synthetic paths shown in FIGS. 5 and 6.

FIG. 5

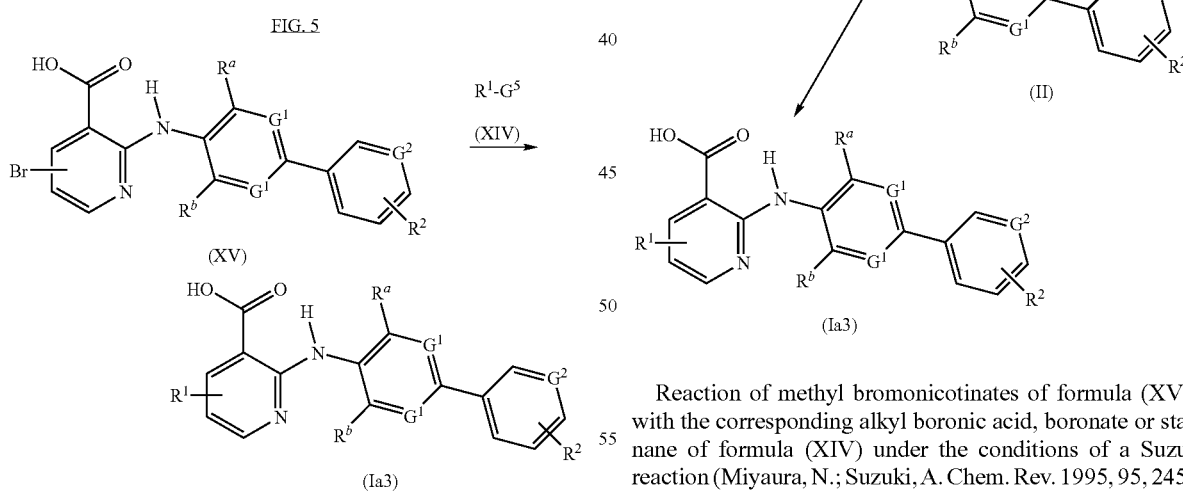

Reaction of the bromonicotinic acids of formula (XV) with the corresponding alkyl boronic acid, boronate or stannane of formula (XIV) under the conditions of a Suzuki reaction (Miyaura, N.; Suzuki, A. Chem. Rev. 1995, 95, 2457) wherein $G^5$ represents boronic acids or boronates or under the conditions of a Stille reaction wherein $G^5$ represents stannanes yield the desired compounds of general formula (Ia3).

FIG. 6

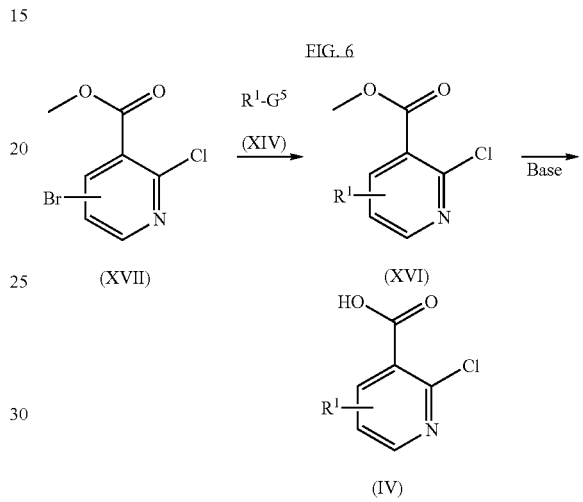

Reaction of methyl bromonicotinates of formula (XVII) with the corresponding alkyl boronic acid, boronate or stannane of formula (XIV) under the conditions of a Suzuki reaction (Miyaura, N.; Suzuki, A. Chem. Rev. 1995, 95, 2457) wherein $G^5$ represents boronic acids or boronates or under the conditions of a Stille reaction wherein $G^5$ represents stannanes, yield the compounds of general formula (XVI). Hydrolisis of the resulting nicotinate of formula (XVI) with a base such as lithium hydroxide or sodium hydroxide in a protic solvent such as methanol or ethanol at a temperature from 0 to 50° C., yields nicotinic acid derivatives of formula (IV). Final compounds of formula (Ia3) may be obtained by the reaction of these nicotinic acids of formula (IV) with the corresponding anilines of formula (II) in acid media such as acetic acid as a solvent or with a high boiling point solvent such as xylene, ethoxyethanol or DMF at a temperature from 100 to 160° C. Alternatively, the reaction can be carried out in basic media such as DBU, DIEA or Cs2CO3 in a high boiling point solvent such as xylene, ethoxyethanol, DMF or NMP.

The syntheses of the compounds of the invention and of the intermediates for use therein are illustrated by the following Examples (1 to 62) including Preparation Examples (Intermediates 1 to 51) which do not limit the scope of the invention in any way.

[1] H Nuclear Magnetic Resonance Spectra were recorded on a Varian Mercury 200 spectrometer. Low Resolution Mass Spectra (m/z) were recorded on a Micromass ZMD mass spectrometer using ESI ionization. The chromatographic separations were obtained using a Waters 2690 system equipped with a Symmetry C18 (2.1×10 mm, 3.5 mM) column. The mobile phase was formic acid (0.4 mL), ammonia (0.1 mL), methanol (500 mL) and acetonitrile (500 mL) (B) and formic acid (0.46 mL), ammonia (0.115 mL) and water (1000 mL) (A): initially 0.5 min with 0% of B, then from 0% to 95% of B in 6.5 min, and then 1 min. with 95% of B. The reequilibration time between two injections was 1 min. The flow rate was 0.4 mL/min. The injection volume was 5 microliter. Diode array chromatograms were collected at 210 nM.

PREPARATION EXAMPLES

Intermediate 1

3'-Ethoxy-3-fluorobiphenyl-4-amine

To a solution of 4-bromo-2-fluoroaniline (3.2 g, 17.05 mmol), 2M $K_2CO_3$ (24 ml, 48.00 mmol), $Pd(PPh_3)_4$ (1.2 g, 1.02 mmol) in toluene (120 ml) under nitrogen atmosphere was added dropwise a solution of the 3-ethoxyphenylboronic acid (4.25 g, 25.61 mmol) in 31 ml of MeOH. The mixture was heated to 80° C. overnight and then cooled to room temperature. Ethyl acetate was added and washed twice with a $K_2CO_3$ aqueous solution. The organic layer was washed with brine, dried over magnesium sulphate, filtered and the solvent evaporated under vacuum. The residue obtained was purified by flash chromatography eluting with Hexane/AcOEt (from 10/1 to 8/1). The solid obtained was recrystallized in hexane to yield 3.78 g of the desired compound as a white solid. Yield=72%

LRMS: m/z 232 (M+1)$^+$.
Retention time: 6.44 min
1H NMR (250 MHz, CDCl$_3$) δ ppm: 1.4 (t, J=6.9 Hz, 3H); 4.1 (q, J=6.9 Hz, 2H); 6.8 (m, 2H); 7.1 (m, 2H); 7.2-7.3 (m, 3H).

Intermediate 2

3-Fluoro-3'-(trifluoromethoxy)biphenyl-4-amine

Obtained (54%) from 4-bromo-2-fluoroaniline and 3-(trifluoromethoxy)phenylboronic acid following the experimental procedure described for intermediate 1.

LRMS: m/z 272 (M+1)$^+$.
Retention time: 6.81 min
$^1$H NMR (250 MHz, CDCl$_3$) δ ppm: 6.8 (m, 1H); 7.2 (m, 3H); 7.4 (m, 3H).

Intermediate 3

3'-Ethoxy-3-(trifluoromethoxy)biphenyl-4-amine

Obtained (40%) from 4-bromo-2-(trifluoromethoxy) aniline and 3-ethoxyphenylboronic acid following the experimental procedure described for intermediate 1.

LRMS: m/z 298 (M+1)$^+$.
Retention time: 7.04 min
$^1$H NMR (200 MHz, CDCl$_3$) δ ppm: 1.4 (t, J=7.0 Hz, 3 H); 3.9 (s, 2 H); 4.1 (q, J=7.0 Hz, 2 H); 6.8 (m, 2 H); 7.1 (m, 2 H); 7.3 (m, 3 H)

Intermediate 4

3-Fluoro-3'-methoxybiphenyl-4-amine

Obtained (35%) from 4-bromo-2-fluoroaniline and 3-methoxyphenylboronic acid following the experimental procedure described for intermediate 1.

LRMS: m/z 218 (M+1)$^+$.
$^1$H NMR (250 MHz, CDCl$_3$) δ ppm: 3.9 (s, 3H); 6.8 (m, 2H); 7.1 (m, 2H); 7.3 (m, 3H)

Intermediate 5

3'-Methoxy-3-(trifluoromethoxy)biphenyl-4-amine

Obtained (56%) from 4-bromo-2-(trifluoromethoxy) aniline and 3-methoxyphenylboronic acid following the experimental procedure described for intermediate 1.

LRMS: m/z 284 (M+1)$^+$.
$^1$H NMR (250 MHz, CDCl$_3$) δ ppm: 3.8 (s, 3H); 6.8 (m, 2H); 7.0 (m, 1H); 7.1 (m, 1H); 7.3-7.4 (m, 3H).

Intermediate 6

2,5-Difluoro-3'-methoxybiphenyl-4-amine

Obtained (84%) from 4-bromo-2,5-difluoroaniline and 3-methoxyphenylboronic acid following the experimental procedure described for intermediate 1.

LRMS: m/z 236 (M+1)$^+$.
Retention time: 6.20 min

Intermediate 7

3'-Ethoxy-2,5-difluorobiphenyl-4-amine

Obtained (66%) from 4-bromo-2,5-difluoroaniline and 3-ethoxyphenylboronic acid following the experimental procedure described for intermediate 1.

LRMS: m/z 250 (M+1)$^+$.
Retention time: 6.58 min

Intermediate 8

2',3-Difluoro-3'-methoxybiphenyl-4-amine

Obtained (54%) from 4-bromo-2-fluoroaniline and 2-fluoro-3-methoxyphenylboronic acid following the experimental procedure described for intermediate 1.

LRMS: m/z 236 (M+1)$^+$
Retention time: 5.93 min
$^1$H NMR (200 MHz, CDCl$_3$) δ ppm: 3.8 (s, 2 H); 3.9 (s, 3 H); 6.9 (m, 3 H); 7.1 (m, 3 H).

Intermediate 9

2-Methyl-3'-(trifluoromethoxy)biphenyl-4-amine

Obtained (86%) from 4-bromo-3-methylaniline and 3-(trifluoromethoxy)phenylboronic acid following the experimental procedure described for intermediate 1.

LRMS: m/z 268 (M+1)$^+$
Retention time: 6.54 min
$^1$H NMR (200 MHz, CDCl$_3$) δ ppm: 2.2 (s, 3 H); 3.7 (s, 2 H); 6.6 (m, 2 H); 7.0 (d, J=8.2 Hz, 1 H); 7.2 (m, 3 H); 7.4 (m, 1 H).

Intermediate 10

3-Chloro-3'-(trifluoromethoxy)biphenyl-4-amine

Obtained (78%) from 4-bromo-2-chloroaniline and 3-(trifluoromethoxy)phenylboronic acid following the experimental procedure described for intermediate 1.
LRMS: m/z 288 (M+1)$^+$
Retention time: 7.12 min
$^1$H NMR (200 MHz, DMSO-D$_6$) δ ppm: 5.6 (s, 2 H); 6.9 (d, J=8.6 Hz, 1 H); 7.2 (m, J=8.2 Hz, 1 H); 7.5 (m, 5 H).

Intermediate 11

3-Chloro-3'-ethoxybiphenyl-4-amine

Obtained (79%) from 4-bromo-2-chloroaniline and 3-ethoxyphenylboronic acid following the experimental procedure described for intermediate 1.
LRMS: m/z 248 (M+1)$^+$
Retention time: 6.75 min
$^1$H NMR (200 MHz, DMSO-D$_6$) δ ppm: 1.3 (t, J=7.0 Hz, 3 H); 4.1 (q, J=7.0 Hz, 2 H); 5.5 (s, 2 H) 6.8 (m, 2 H); 7.1 (m, 2 H); 7.3 (t, J=7.8 Hz, 1 H); 7.4 (dd, J=8.4, 2.1 Hz, 1 H); 7.5 (d, =2.3 Hz, 1 H).

Intermediate 12

3'-Ethoxybiphenyl-4-amine

Obtained (91%) from 4-bromoaniline and 3-ethoxyphenylboronic acid following the experimental procedure described for intermediate 1.
LRMS: m/z 214 (M+1)$^+$
Retention time: 5.73 min
$^1$H NMR (200 MHz, CDCl$_3$) δ ppm: 1.4 (t, J=7.0 Hz, 3 H); 3.7 (s, 2 H); 4.1 (q, J=7.0 Hz, 2 H); 6.8 (m, 3 H); 7.1 (m, 2 H); 7.4 (m, 3 H).

Intermediate 13

3-Methyl-3'-(trifluoromethoxy)biphenyl-4-amine

Obtained (83%) from 4-bromo-2-methylaniline and 3-(trifluoromethoxy)phenylboronic acid following the experimental procedure described for intermediate 1.
LRMS: m/z 268 (M+1)$^+$
Retention time: 6.82 min
$^1$H NMR (200 MHz, CDCl$_3$) δ ppm: 2.2 (s, 3 H); 3.7 (s, 2 H); 6.7 (d, J=9.0 Hz, 1 H); 7.1 (m, J=7.8 Hz, 1 H); 7.4 (m, 5 H).

Intermediate 14

3-Chloro-3'-methoxybiphenyl-4-amine

Obtained (87%) from 4-bromo-2-chloroaniline and 3-methoxyphenylboronic acid following the experimental procedure described for intermediate 1.
LRMS: m/z 234 (M+1)$^+$
Retention time: 6.44 min
$^1$H NMR (200 MHz, CDCl$_3$) δ ppm: 3.9 (s, 3 H); 4.1 (s, 2 H); 6.8 (m, 2 H); 7.1 (m, 2 H); 7.3 (m, 2 H); 7.5 (d, J=2.3 Hz, 1 H).

Intermediate 15

3'-(Difluoromethoxy)-3-fluorobiphenyl-4-amine

Obtained (76%) from 4-bromo-2-fluoroaniline and 2-(3-(difluoromethoxy)phenyl)-4,4,5,5-tetramethyl-1,3,2-dioxaborolane following the experimental procedure described for intermediate 1.
LRMS: m/z 254 (M+1)$^+$
Retention time: 6.24 min
$^1$H NMR (200 MHz, CDCl$_3$) δ ppm: 3.9 (s, 2 H); 6.5 (t, J=73.8 Hz, 1 H); 6.8 (m, 1 H); 7.1 (m, 1 H); 7.3 (m, 3 H); 7.4 (m, 2 H).

Intermediate 16

Methyl 2-(3-fluoro-3'-hydroxybiphenyl-4-ylamino)nicotinate

To a mixture of 2-(3-fluoro-3'-hydroxybiphenyl-4-ylamino)nicotinic acid (1 g, 3.08 mmol) and NaHCO$_3$ (0.5 g, 6.17 mmol) in acetone (20 ml) was added dropwise dimethyl sulphate (0.47 g, 3.70 mmol). The mixture was heated to reflux overnight and then concentrated. Ethyl acetate was added to the crude and washed twice with 4% solution of NaHCO$_3$ and brine. The organic phase was then dried over MgSO$_4$ and concentrated in vacuo to afford 0.4 g of solid beige pure enough for the next synthetic step. Yield=36%
LRMS: m/z 339 (M+1)$^+$.
Retention time: 7.02 min Intermediate 17

Methyl 2-(3,5-difluoro-3'-hydroxybiphenyl-4-ylamino)nicotinate

Obtained (52%) from 2-(3,5-difluoro-3'-hydroxybiphenyl-4-ylamino)nicotinic acid following the experimental procedure described for intermediate 16.
LRMS: m/z 357 (M+1)$^+$.
Retention time: 6.26 min Intermediate 18

Methyl 2-(3-fluoro-3'-(2,2,2-trifluoroethoxy)biphenyl-4-ylamino)nicotinate

A mixture of intermediate 16 (0.36 g, 1.06 mmol), 2-bromo-1,1,1-trifluoroethane (0.26 g, 1.6 mmol) and potassium carbonate (0.29 g, 2.13 mmol) in DMF was stirred at 120° C. under a nitrogen atmosphere overnight. Water was added and the mixture extracted with EtOAc (2×). The combined organic phase was washed with water and brine, dried over MgSO$_4$ and concentrated in vacuo. Purification by column chromatography (10% EtOAc in hexanes) afforded the desired compound as a yellow solid. Yield=27%
LRMS: m/z 421 (M+1)$^+$.
Retention time: 7.73 min

Intermediate 19

Methyl 2-(3'-cyclobutoxy-3-fluorobiphenyl-4-ylamino)nicotinate

Obtained (48%) from intermediate 16 and bromocyclobutane following the experimental procedure described for intermediate 18.

LRMS: m/z 393 (M+1)$^+$.

Retention time: 8.08 min

Intermediate 20

Methyl 2-(3'-cyclobutoxy-3,5-difluorobiphenyl-4-ylamino)nicotinate

Obtained (26%) from intermediate 17 and bromocyclobutane following the experimental procedure described for intermediate 18.

LRMS: m/z 411 (M+1)$^+$.

Retention time: 7.53 min

Intermediate 21

2-(4-Bromo-2,6-difluorophenylamino)nicotinic acid

A mixture of 2-chloronicotinic acid (1.6 g, 10.15 mmol) and 4-bromo-2,6-difluoroaniline (3.24 g, 15.58 mmol) in acetic acid (40 ml) was heated overnight at 130° C. under nitrogen atmosphere. The mixture was cooled to room temperature to give a precipitate. The mixture was filtered, and the solid was rinsed with acetic acid to afford 2-hydroxynicotinic acid (side-product). A second solid precipitate when the filtrate was partially concentrated to give another precipitate which corresponds to N-(4-bromo-2,6-difluorophenyl)acetamide (another side-product). Finally the filtrate was concentrated to dryness and 3.14 g of the desired compound was obtained as a solid, containing some acetamide but the mixture was used to perform the next synthetic step.

LRMS: m/z 329, 331 (M+1)$^+$.

Retention time: 6.09 min

Intermediate 22

Methyl 3-(3'-ethoxy-3-fluorobiphenyl-4-ylamino)isonicotinate

A mixture of methyl 3-chloroisonicotinate (1.00 g, 5.83 mmol), intermediate 1 (1.35 g, 5.83 mmol), Cs$_2$CO$_3$ (2.66 g, 8.16 mmol) and Xantphos (0.68 g, 1.17 mmol) in dioxane (20 mL) was stirred under argon atmosphere for 10 min. Then Pd$_2$(dba)$_3$ (0.53 g, 0.58 mmol) was added and the mixture stirred under argon atmosphere at 120° C. overnight. The reaction mixture was filtered over Celite and washed with CH$_2$Cl$_2$. The filtrate was concentrated and purified by column chromatography eluting with EtOAc/hexane/Et3N (20/79/1) and the desired compound was obtained. Yield=51%

LRMS: m/z 367 (M+1)$^+$.

$^1$H NMR (250 MHz, CDCl$_3$) δ ppm: 9.26 (s, 1H); 8.8 (s, 1H); 8.25 (d, J=5.3 Hz, 1H); 7.87 (d, J=5.3 Hz, 1H); 7.72-7.45 (m, 4H); 7.3 (d, J=8.2 Hz, 1H); 7.26 (s, 1H); 7.05 (dd, J=8.2, J=1.8 Hz, 1H); 4.25 (c, J=7 Hz, 2H); 4.12 (s, 3H); 1.61 (t, J=7 Hz, 3H).

Intermediate 23

Methyl 3-(3-fluoro-3'-methoxybiphenyl-4-ylamino)isonicotinate

Obtained (57%) from methyl 3-chloroisonicotinate and intermediate 4 following the experimental procedure described for intermediate 22.

LRMS: m/z 353 (M+1)$^+$.

$^1$H NMR (250 MHz, CDCl$_3$) δ ppm: 9.11 (s, 1H); 8.65 (s, 1H); 8.1 (d, J=4.9 Hz, 1H); 7.72 (d, J=5.2 Hz, 1H); 7.58-7.27 (m, 4H); 7.16 (d, J=7.4 Hz, 1H); 7.1 (t, J=1.7 Hz, 1H); 6.9 (dd, J=8.2, J=2.5 Hz, 1H); 3.96 (s, 3H); 3.87 (s, 3H).

Intermediate 24

Methyl 3-(3% methoxy-3-(trifluoromethoxy)biphenyl-4-ylamino)isonicotinate

Obtained (76%) from methyl 3-chloroisonicotinate and intermediate 5 following the experimental procedure described for intermediate 22.

LRMS: m/z 419 (M+1)$^+$.

$^1$H NMR (250 MHz, CDCl$_3$) δ ppm: 9.44 (s, 1H); 8.95 (s, 1H); 8.3 (d, J=5.2 Hz, 1H); 7.9 (d, J=4.9 Hz, 1H); 7.72 (m, 3H); 7.53 (m, 1H); 7.32 (d, J=8.2 Hz, 1H); 7.27 (m, 1H); 7.07 (d, J=9 Hz, 1H); 4.12 (s, 3H); 4.03 (s, 3H).

Intermediate 25

Methyl 3-(3-fluoro-3'-(trifluoromethoxy)biphenyl-4-ylamino)isonicotinate

Obtained (92%) from methyl 3-chloroisonicotinate and intermediate 2 following the experimental procedure described for intermediate 22.

LRMS: m/z 407 (M+1)$^+$.

$^1$H NMR (250 MHz, CDCl$_3$) δ ppm: 8.98 (s, 1H); 8.5 (s, 1H); 7.95 (d, J=4.9 Hz, 1H); 7.58 (d, J=4.9 Hz, 1H); 7.46-7.15 (m, 6H); 7.06 (m, 1H); 3.81 (s, 3H).

Intermediate 26

3'-Ethoxy-5-fluoro-2-methylbiphenyl-4-amine

Obtained (80%) from 4-bromo-2-fluoro-5-methylaniline and 3-ethoxyphenylboronic acid following the experimental procedure described for intermediate 1.

LRMS: m/z 246 (M+1)$^+$

Retention time: 6.36 min $^1$H NMR (200 MHz, CDCl$_3$) δ ppm: 1.4 (t, J=6.8 Hz, 3 H); 2.2 (s, 3 H); 3.7 (s, 2 H); 4.1 (q, J=7.0 Hz, 2 H); 6.7 (d, J=9.0 Hz, 1 H); 6.9 (m, 4 H); 7.3 (m, 1 H)

Intermediate 27

5-Fluoro-2-methyl-3'-(trifluoromethoxy)biphenyl-4-amine

Obtained (92%) from 4-bromo-2-fluoro-5-methylaniline and 3-(trifluoromethoxy)phenylboronic acid following the experimental procedure described for intermediate 1.

LRMS: m/z 286 (M+1)$^+$

Retention time: 6.96 min $^1$H NMR (200 MHz, CDCl$_3$) δ ppm: 2.2 (s, 3 H); 3.7 (s, 2 H); 6.7 (d, J=9.0 Hz, 1 H); 6.9 (d, J=11.7 Hz, 1 H); 7.2 (m, 3 H); 7.4 (m, 1 H).

Intermediate 28

2',3-Difluoro-5'-isopropoxybiphenyl-4-amine

Obtained (95%) from 4-bromo-2-fluoroaniline and 2-fluoro-5-isopropoxyphenylboronic acid following the experimental procedure described for intermediate 1.
LRMS: m/z 264 (M+1)$^+$
Retention time: 6.67 min
$^1$H NMR (200 MHz, CDCl$_3$) δ ppm: 1.3 (d, J=6.2 Hz, 6 H); 3.8 (s, 2 H); 4.5 (m, 1 H); 6.8 (m, 3 H); 7.0 (m, 1 H); 7.2 (m, 2 H).

Intermediate 29

3,5-Difluoro-3'-methoxybiphenyl-4-amine

Obtained (91%) from 4-bromo-2,6-difluoroaniline and 3-methoxyphenylboronic acid following the experimental procedure described for intermediate 1.
LRMS: m/z 236 (M+1)$^+$
Retention time: 6.34 min
$^1$H NMR (200 MHz, CDCl$_3$) δ ppm: 3.8 (s, 2 H); 3.9 (s, 3 H); 6.9 (m, 1 H); 7.1 (m, 4 H); 7.3 (t, J=8.0 Hz, 1 H)

Intermediate 30

5-Fluoro-3'-methoxy-2-methylbiphenyl-4-amine

Obtained (80%) from 4-bromo-2-fluoro-5-methylaniline and 3-methoxyphenylboronic acid following the experimental procedure described for intermediate 1.
LRMS: m/z 232 (M+1)$^+$
Retention time: 6.00 min
$^1$H NMR (200 MHz, DMSO-D$_6$) δ ppm: 2.1 (s, 3 H); 3.7 (s, 3 H); 5.1 (s, 2 H); 6.6 (d, J=9.4 Hz, 1 H); 6.8 (m, 4 H); 7.3 (t, J=7.8 Hz, 1 H)

Intermediate 31

Methyl 2-chloro-5-methylnicotinate

To a solution of methyl 5-bromo-2-chloronicotinate (1.05 g, 4.19 mmol), K$_3$PO$_4$ (2.95 g, 13.90 mmol), methylboronic acid (0.32 g, 5.26 mmol) and tricyclohexylphosphine (0.11 g, 0.39 mmol) in toluene/water (16 ml/0.8 ml) under nitrogen atmosphere was added Pd(OAc)$_2$ (0.04 g, 0.18 mmol). The mixture was heated at 100° C. overnight under nitrogen atmosphere. The reaction mixture was then cooled to room temperature and concentrated in vacuum. Ethyl acetate was added to the residue and this organic layer was washed with water, brine, dried over MgSO$_4$, filtered and the solvent evaporated under vacuum to yield the desired product as a yellow oil. Yield=87%
LRMS: m/z 186 (M+1)$^+$
Retention time: 4.84 min

Intermediate 32

2-Chloro-5-methylnicotinic acid

Intermediate 31 (0.38 g, 1.81 mmol) was dissolved in MeOH (2 ml) and 2N NaOH solution was added (1.81 ml, 3.62 mmol) and the mixture stirred at room temperature for 2 hours. The reaction mixture was concentrated to dryness and the residue redissolved in EtOAc/water. The organic layer was separated, dried over magnesium sulphate and concentrated in vacuum to yield the desired product as a white solid. Yield=94%
LRMS: m/z 172 (M+1)$^+$
Retention time: 3.25 min
$^1$H NMR (200 MHz, DMSO-D$_6$) δ ppm: 2.2 (s, 3 H); 7.6 (d, J=2.53 Hz, 1 H); 8.0 (d, J=2.53 Hz, 1 H)

Intermediate 33

Methyl 2-(3'-(cyclopropylmethoxy)-3,5-difluorobiphenyl-4-ylamino)nicotinate

Obtained (83%) from intermediate 17 and bromocyclobutane following the experimental procedure described for intermediate 18.
LRMS: m/z 411 (M+1)$^+$.
Retention time: 7.48 min

Intermediate 34

5-bromo-2-(3'-ethoxy-3,5-difluorobiphenyl-4-ylamino)nicotinic acid

A mixture of 5-bromo-2-chloronicotinic acid (1.42 g, 6.01 mmol), intermediate 21 (1.0 g, 4.01 mmol) and p-toluenesulfonic acid (0.5 g, 2.42 mmol) in water (10 ml) was heated overnight at 110° C. under nitrogen atmosphere. The reaction mixture was cooled to room temperature and a precipitate was formed. The solid formed was filtered, washed with hot water and then with cold MeOH. The solid was finally washed with diisopropylether and dried in a vacuum oven. Yield=63%.
LRMS: m/z 449, 451 (M+1)$^+$.
Retention time: 7.52 min

Intermediate 35

5-bromo-2-(5-fluoro-3'-methoxy-2-methylbiphenyl-4-ylamino)nicotinic acid

Obtained (73%) from intermediate 30 and 5-bromo-2-chloronicotinic acid following the experimental procedure described for intermediate 34.
LRMS: m/z 431,433 (M+1)$^+$.
Retention time: 7.98 min

Intermediate 36

1-bromo-3-cyclopropoxybenzene

A mixture of 3-bromophenol (2.4 g, 13.9 mmol), bomocyclopropane (6.66 ml, 83 mmol) and potassium carbonate (9.6 g, 69.5 mmol) in DMF (16 ml) was heated at 180° C. in a microwave oven for 8 hours. The reaction mixture was diluted with a mixture of diethylether and water. The organic layer was separated, washed with water, brine, dried over Na$_2$SO$_4$, filtered and evaporated. An oil was obtained, 2.87 g, with a purity of 81%.
This intermediate was used for the next reaction.
Retention time: 6.91 min.

Intermediate 37

2-(3-cyclopropoxyphenyl)-4,4,5,5-tetramethyl-1,3,2-dioxaborolane

A mixture of intermediate 36 (2.87 g, 10.9 mmol), bis(pinacolato)diboron (4.16 g, 16.4 mmol) and potassium acetate (3.2 g, 32.7 mmol) in anhydrous dioxane, was stirred under nitrogen atmosphere and then $PdCl_2dppf \cdot CH_2Cl_2$ (0.5 g, 0.55 mmol) was added. The reaction mixture was heated at 100° C. for 3 h. The crude was then filtered over celite, washed with dioxane and evaporated under reduce pressure. The residue obtained was purified by reverse-phase chromatography eluting with a gradient of water and AcN/MeOH (1/1) (from 0% to 100% of AcN/MeOH(1/1)). The desired product was obtained as a yellow oil.

Yield=55%.
LRMS: m/z 261 (M+1)+.
Retention time: 7.23 min

Intermediate 38

3,5-difluoro-2-methylbiphenyl-4-amine

Obtained (92%) from 4-bromo-2,6-difluoro-3-methylaniline and phenylboronic acid following the experimental procedure described for intermediate 1.
LRMS: m/z 220 (M+1)+.
Retention time: 6.73 min

Intermediate 39

5-bromo-2-(2,5-difluoro-3'-methoxybiphenyl-4-ylamino)nicotinic acid

Obtained (78%) from intermediate 6 and 5-bromo-2-chloronicotinic acid following the experimental procedure described for intermediate 34.
LRMS: m/z 433,435 (M+1)+.
Retention time: 7.77 min

Intermediate 40

Methyl 2-chloro-5-cyclopropylnicotinate

Obtained (99%) from methyl 5-bromo-2-chloronicotinate and cyclopropylboronic acid following the experimental procedure described for intermediate 31.
LRMS: m/z 212 (M+1)+.
Retention time: 5.46 min

Intermediate 41

2-chloro-5-cyclopropylnicotinic acid

Obtained (65%) from intermediate 40 following the experimental procedure described for intermediate 32.
LRMS: m/z 198 (M+1)+.
Retention time: 4.29 min

Intermediate 42

2-(4-bromo-2,6-difluorophenylamino)-5-cyclopropylnicotinic acid

Obtained (65%) from intermediate 41 and 4-bromo-2,6-difluoroanline following the experimental procedure described for intermediate 34.
LRMS: m/z 369,371 (M+1)+.
Retention time: 7.06 min

Intermediate 43

2,3,5-trifluoro-3'-methoxybiphenyl-4-amine

Obtained (60%) from 4-bromo-2,3,6-trifluoroaniline and 3-methoxyphenylboronic acid following the experimental procedure described for intermediate 1.
LRMS: m/z 254 (M+1)+
Retention time: 6.45 min

Intermediate 44

4-bromo-2,6-difluoro-3-methylaniline

To a solution of 2,6-difluoro-3-methylaniline (5 g, 34.9 mmol) in acetic acid (50 ml) was added dropwise a solution of bromine (1.97 ml, 38.4 mmol) in acetic acid (10 ml) at 55° C. The reaction mixture was stirred for 1 hour and then poured to water/ice. A solid was filtered, washed with water and dried in a vacuum oven. 6.3 g of a black solid were obtained (yield=81%).
Retention time: 6.28 min

Intermediate 45

2-(4-bromo-2,6-difluoro-3-methylphenylamino)nicotinic acid

Obtained (46%) from intermediate 44 and 2-chloronicotinic acid following the experimental procedure described for intermediate 34.
LRMS: m/z 343,345 (M+1)+.
Retention time: 6.50 min

Intermediate 46

2-(4-bromo-2,6-difluorophenylamino)-5-chloronicotinic acid

Obtained (36%) from 4-bromo-2,6-difluoroaniline and 2,5-dichloronicotinic acid following the experimental procedure described for intermediate 34.
LRMS: m/z 363,365 (M+1)+
Retention time: 7.09 min

Intermediate 47

2,3,5,6-tetrafluoro-3'-methoxybiphenyl-4-amine

Obtained (91%) from 4-bromo-2,3,5,6-tetrafluoroaniline and 3-methoxyphenylboronic acid following the experimental procedure described for intermediate 1.
LRMS: m/z 272 (M+1)+
Retention time: 6.49 min

Intermediate 48

Methyl 3-(2-fluorophenylamino)isonicotinate

Obtained (34%) from methyl 3-chloroisonicotinate and 2-fluoroaniline following the experimental procedure described for intermediate 22.
LRMS: m/z 247 (M+1)+

Intermediate 49

Methyl 3-(4-bromo-2-fluorophenylamino)isonicotinate

Obtained (90%) from intermediate 48 following the experimental procedure described for intermediate 44.

LRMS: m/z 323,325 (M+1)$^+$ $^1$H NMR (250 MHz, CDCl$_3$) δ ppm: 3.9 (s, 3H); 7.3 (m, 3H); 7.7 (d, J=7.5 Hz, 1H); 8.1 (d, J=7.5 Hz, 1H); 8.5 (s, 1H); 9.0 (s, 1H).

Intermediate 50

Methyl 3-(2'-chloro-3-fluorobiphenyl-4-ylamino)isonicotinate

Obtained (29%) from intermediate 49 and 2-chlorophenylboronic acid following the experimental procedure described for intermediate 1.

LRMS: m/z 357 (M+1)$^+$.

Intermediate 51

Methyl 3-(3'-cyclopropoxy-3-fluorobiphenyl-4-ylamino)isonicotinate

Obtained (56%) from intermediate 50 and 2-(3-cyclopropoxyphenyl)-4,4,5,5-tetramethyl-1,3,2-dioxaborolane following the experimental procedure described for intermediate 1.

LRMS: m/z 379 (M+1)$^+$
Retention time: 7.44 min

PREPARATION EXAMPLES

Example 1

2-(3-Fluoro-3'-methoxybiphenyl-4-ylamino)nicotinic acid

A mixture of 2-chloronicotinic acid (4.86 g, 30.89 mmol) and intermediate 4 (10.06 g, 46.34 mmol) in acetic acid (160 ml) was heated overnight at 130° C. under nitrogen atmosphere. The reaction mixture was cooled to room temperature and a precipitate was formed. The yellow solid formed was filtered, washed with acetic and diethyl ether and dried in a vacuum oven. Yield=65%.

$^1$H NMR (200 MHz, CD$_3$OD) δ ppm: 3.9 (s, 3H); 7.0 (m, 1H); 7.21 (m, 3H); 7.41 (t, 1H); 7.71 (m, 3H); 8.15 (dd, J=6.05, 1.76 Hz, 1H); 8.83 (dd, J=7.61, 1.76 Hz, 1H).
LRMS: m/z 339 (M+1)$^+$.
Retention time: 7.09 min

Example 2

2-(3'-Ethoxy-3-fluorobiphenyl-4-ylamino)nicotinic acid

Obtained (43%) from 2-chloronicotinic acid and intermediate 1 following the experimental procedure described in example 1.

$^1$H NMR (400 MHz, DMSO-D$_6$) δ ppm: 1.4 (t, J=6.9 Hz, 3 H); 4.1 (q, J=6.9 Hz, 2 H); 6.9 (d, J=8.3 Hz, 1 H); 7.0 (m, 1 H); 7.2 (d, J=1.7 Hz, 1 H); 7.3 (d, J=7.8 Hz, 1 H); 7.4 (t, J=7.8 Hz, 1 H); 7.5 (d, J=8.3 Hz, 1 H); 7.7 (d, J=12.8 Hz, 1 H); 8.3 (m, 1 H); 8.5 (m, 1 H); 8.7 (t, J=8.8 Hz, 1 H); 10.8 (s, 1 H)
LRMS: m/z 353 (M+1)$^+$.
Retention time: 7.39 min

Example 3

2-(3-Fluoro-3'-(trifluoromethoxy)biphenyl-4-ylamino)nicotinic acid

Obtained (37%) from intermediate 2 and 2-chloronicotinic acid following the experimental procedure described in example 1.

$^1$H NMR (200 MHz, DMSO-D$_6$) δ ppm: 7.0 (dd, J=7.8, 4.7 Hz, 1 H); 7.4 (d, J=8.2 Hz, 1 H); 7.7 (m, 5 H); 8.3 (dd, J=7.8, 2.0 Hz, 1 H); 8.5 (dd, J=4.7, 2.0 Hz, 1 H); 8.8 (t, J=8.8 Hz, 1 H); 10.8 (d, J=3.1 Hz, 1 H)
LRMS: m/z 393 (M+1)$^+$
Retention time: 7.63 min

Example 4

2-(3'-Ethoxy-3-(trifluoromethoxy)biphenyl-4-ylamino)nicotinic acid

Obtained (18%) from intermediate 3 and 2-chloronicotinic acid following the experimental procedure described in example 1.

$^1$H NMR (200 MHz, DMSO-D$_6$) δ ppm: 1.4 (t, J=7.0 Hz, 3 H); 4.1 (q, J=7.0 Hz, 2 H); 7.0 (m, 2 H); 7.3 (m, 3 H); 7.7 (m, 2 H); 8.3 (m, 1 H); 8.5 (m, 1 H); 8.9 (d, J=8.6 Hz, 1 H); 11.2 (s, 1 H).
LRMS: m/z 417 (M−1)$^-$.
Retention time: 7.65 min

Example 5

2-(3'-Methoxy-3-(trifluoromethoxy)biphenyl-4-ylamino)nicotinic acid

Obtained (14%) from intermediate 5 and 2-chloronicotinic acid following the experimental procedure described in example 1.

LRMS: m/z 405 (M+1)$^+$.
Retention time: 7.44 min

Example 6

2-(2,5-Difluoro-3'-methoxybiphenyl-4-ylamino)nicotinic acid

Obtained (12%) from intermediate 6 and 2-chloronicotinic acid following the experimental procedure described in example 1.

$^1$H NMR (200 MHz, DMSO-D$_6$) δ ppm: 3.8 (s, 3 H); 7.0 (m, 4 H); 7.4 (t, J=8.0 Hz, 1 H); 7.6 (dd, J=12.1, 7.4 Hz, 1 H); 8.3 (dd, J=7.8, 2.0 Hz, 1 H); 8.5 (dd, J=4.7, 2.0 Hz, 1 H); 8.7 (dd, J=13.7, 7.0 Hz, 1 H); 11.0 (s, 1 H).
LRMS: m/z 357 (M+1)$^+$.
Retention time: 7.35 min

Example 7

2-(3'-Ethoxy-2,5-difluorobiphenyl-4-ylamino)nicotinic acid

Obtained (36%) from intermediate 7 and 2-chloronicotinic acid following the experimental procedure described in example 1.

$^1$H NMR (200 MHz, DMSO-D$_6$) δ ppm: 1.4 (t, J=6.9 Hz, 3 H); 4.1 (q, J=6.9 Hz, 2 H); 7.0 (m, 4 H); 7.4 (t, J=7.8 Hz, 1 H);

7.6 (dd, J=12.3, 7.2 Hz, 1 H); 8.3 (dd, J=7.4, 2.0 Hz, 1 H); 8.5 (dd, J=5.1, 2.0 Hz, 1 H); 8.7 (dd, J=13.7, 7.0 Hz, 1 H); 11.0 (s, 1 H).
LRMS: m/z 371 (M+1)$^+$.
Retention time: 7.51 min

Example 8

2-(2',3-Difluoro-3'-methoxybiphenyl-4-ylamino) nicotinic acid

Obtained (31%) from intermediate 8 and 2-chloronicotinic acid following the experimental procedure described in example 1.
$^1$H NMR (200 MHz, DMSO-D$_6$): δ ppm 3.9 (s, 3 H); 7.1 (m, 4 H); 7.4 (m, 2 H); 8.3 (dd, J=7.8, 2.0 Hz, 1 H); 8.5 (dd, J=4.9, 1.8 Hz, 1 H); 8.7 (t, J=8.8 Hz, 1 H); 10.8 (d, J=2.7 Hz, 1 H).
LRMS: m/z 357 (M+1)$^+$.
Retention time: 7.04 min

Example 9

2-(2-Methyl-3'-(trifluoromethoxy)biphenyl-4-ylamino)nicotinic acid

Obtained (61%) from intermediate 9 and 2-chloronicotinic acid following the experimental procedure described in example 1.
$^1$H NMR (200 MHz, CDCl$_3$): δ ppm 2.3 (s, 3 H); 6.8 (dd, J=7.8, 4.7 Hz, 1 H); 7.2 (m, 4 H) 7.5 (m, 3 H); 8.4 (m, 2 H); 10.0 (s, 1 H)
LRMS: m/z 389 (M+1)$^+$.
Retention time: 7.51 min

Example 10

2-(3-Chloro-3'-(trifluoromethoxy)biphenyl-4-ylamino)nicotinic acid

Obtained (44%) from intermediate 10 and 2-chloronicotinic acid following the experimental procedure described in example 1.
$^1$H NMR (200 MHz, CDCl$_3$): δ ppm 6.9 (dd, J=7.8, 5.1 Hz, 1 H); 7.3 (m, 2 H); 7.5 (m, 3 H); 7.7 (d, J=2.0 Hz, 1 H); 8.4 (dd, J=7.8, 2.0 Hz, 1 H); 8.5 (dd, J=4.7, 2.0 Hz, 1 H); 8.8 (d, J=8.6 Hz, 1 H); 10.6 (s, 1 H).
LRMS: m/z 409 (M+1)$^+$
Retention time: 7.74 min

Example 11

2-(3-Chloro-3'-ethoxybiphenyl-4-ylamino)nicotinic acid

Obtained (48%) from intermediate 11 and 2-chloronicotinic acid following the experimental procedure described in example 1.
$^1$H NMR (200 MHz, CDCl$_3$): δ ppm 1.5 (t, J=6.9.0 Hz, 3 H); 4.1 (q, J=6.9 Hz, 2 H); 6.9 (m, 2 H); 7.1 (m, 2 H); 7.3 (t, J=7.8 Hz, 1 H); 7.5 (dd, J=8.6, 2.0 Hz, 1 H); 7.7 (d, J=2.3 Hz, 1 H); 8.4 (dd, J=7.8, 2.3 Hz, 1 H); 8.5 (dd, J=4.7, 2.0 Hz, 1 H); 8.7 (d, J=9.0 Hz, 1 H); 10.5 (s, 1 H)
LRMS: m/z 369 (M+1)$^+$
Retention time: 7.57 min

Example 12

2-(3-Methyl-3'-(trifluoromethoxy)biphenyl-4-ylamino)nicotinic acid

Obtained (41%) from intermediate 13 and 2-chloronicotinic acid following the experimental procedure described in example 1.
$^1$H NMR (200 MHz, CDCl$_3$): δ ppm 2.4 (s, 3 H); 6.8 (m, J=7.8, 4.7 Hz, 1 H); 7.2 (m, J=1.6 Hz, 1 H); 7.3 (m, 1 H); 7.5 (m, 4 H); 8.2 (d, J=9.4 Hz, 1 H); 8.3 (dd, J=7.8, 2.0 Hz, 1 H); 8.4 (dd, J=4.7, 2.0 Hz, 1 H); 10.0 (s, 1 H).
LRMS: m/z 389 (M+1)$^+$
Retention time: 7.62 min

Example 13

2-(3-Chloro-3'-methoxybiphenyl-4-ylamino)nicotinic acid

Obtained (36%) from intermediate 14 and 2-chloronicotinic acid following the experimental procedure described in example 1.
$^1$H NMR (200 MHz, CDCl$_3$): δ ppm 3.9 (s, 3 H); 6.9 (m, 2 H); 7.1 (m, 2 H); 7.4 (m, 1 H); 7.5 (dd, J=8.6, 2.3 Hz, 1 H); 7.7 (d, J=2.0 Hz, 1 H); 8.4 (dd, J=7.8, 2.0 Hz, 1 H); 8.5 (dd, J=4.9, 2.1 Hz, 1 H); 8.7 (d, J=8.6 Hz, 1 H); 10.5 (s, 1 H).
LRMS: m/z 355 (M+1)$^+$
Retention time 7.53 min

Example 14

2-(3'-(Difluoromethoxy)-3-fluorobiphenyl-4-ylamino)nicotinic acid

Obtained (10%) from intermediate 15 and 2-chloronicotinic acid following the experimental procedure described in example 1.
$^1$H NMR (200 MHz, DMSO-D$_6$): δ ppm 7.0 (dd, J=7.6, 4.7 Hz, 1 H); 7.2 (d, J=7.8 Hz, 1 H); 7.3 (t, J=74.1 Hz, 1H); 7.6 (m, 5 H); 8.3 (dd, J=7.8, 2.0 Hz, 1 H); 8.5 (dd, J=4.7, 2.0 Hz, 1 H); 8.7 (t, J=8.8 Hz, 1 H); 10.9 (s, 1 H).
LRMS: m/z 375 (M+1)$^+$
Retention time: 7.43 min

Example 15

2-(3'-Cyclobutoxy-3-fluorobiphenyl-4-ylamino)nicotinic acid

Intermediate 19 (0.28 g, 0.63 mmol) was dissolved in MeOH (10 ml) and 2N NaOH (2 ml) was added. The mixture was stirred overnight at room temperature. The reaction mixture was concentrated and purified by reverse phase column chromatography to afford the desired compound as a yellow solid. Yield=12%
LRMS: m/z 379 (M+1)$^+$.
Retention time: 7.68 min
$^1$H NMR (200 MHz, CD$_3$OD): δ ppm 1.8 (m, 2 H); 2.1 (m, 2 H); 2.5 (m, 2 H); 4.7 (m, 1 H); 6.8 (m, 2 H); 7.2 (m, 5 H); 8.4 (m, J=7.8 Hz, 2 H); 8.6 (t, J=8.4 Hz, 1 H)

Example 16

2-(3-Fluoro-3'-(2,2,2-trifluoroethoxy)biphenyl-4-ylamino)nicotinic acid

Obtained (57%) from intermediate 18 following experimental procedure described in example 15.

LRMS: m/z 407 (M+1)⁺.
Retention time: 7.36 min
¹H NMR (200 MHz, CD₃OD): δ ppm 4.5 (q, J=8.6 Hz, 2 H); 6.8 (m, 2 H); 7.3 (m, 5 H); 8.3 (m, 2 H); 8.6 (t, J=8.8 Hz, 1 H).

Example 17

2-(3'-Cyclobutoxy-3,5-difluorobiphenyl-4-ylamino)nicotinic acid

Obtained (55%) from intermediate 20 following experimental procedure described in example 15.
LRMS: m/z 397 (M+1)⁺.
Retention time: 6.87 min
¹H NMR (200 MHz, DMSO-D₆): δ ppm 1.8 (m, 2 H); 2.1 (m, 2 H); 2.5 (m, 2 H); 4.9 (m, 1 H); 6.9 (t, J=6.4 Hz, 2 H); 7.2 (s, 1 H); 7.4 (m, 2 H); 7.6 (d, J=9.4 Hz, 2 H); 8.3 (d, J=4.3 Hz, 2 H); 9.7 (s, 1 H)

Example 18

2-(3,5-Difluoro-3'-(trifluoromethoxy)biphenyl-4-ylamino)nicotinic acid

To a mixture of intermediate 21 (0.2 g, 0.61 mmol), 3-(trifluoromethoxy)phenylboronic acid (0.19 g, 0.91 mmol), potassium carbonate (0.17 g, 1.21 mmol) in 11 ml of dioxane/water (10/1) was added, under nitrogen atmosphere, Pd(PPh₃)₄ (0.25 g, 0.22 mmol). The mixture was heated to reflux overnight, then filtered over celite and washed with ethyl acetate. The organic phase was washed twice with water, washed with brine, dried over magnesium sulphate, filtered and evaporated under vacuum to give an oil. This crude was purified by preparative HPLC to give a white solid, 60 mg, of the desired compound. Yield=24%
¹H NMR (200 MHz, DMSO-D₆): δ ppm 6.9 (m, 1H); 7.4 (m, 1H); 7.6 (m, 3H); 7.8 (m, 2H); 8.2 (m, 2H)
LRMS: m/z 409 (M−1)⁻
Retention time: 7.27 min.

Example 19

2-(3'-Ethoxy-3,5-difluorobiphenyl-4-ylamino)nicotinic acid

Obtained (28%) from intermediate 21 and 3-ethoxyphenylboronic acid, following the experimental procedure described in example 18.
¹H NMR (200 MHz, DMSO-D₆); δ ppm 1.4 (t, J=6.9 Hz, 3 H); 4.1 (q, J=6.9 Hz, 2 H); 6.9 (dd, J=7.8, 4.7 Hz, 1 H); 7.0 (m, 1 H); 7.4 (m, 5 H); 8.2 (m, 2 H); 9.5 (s, 1 H).
LRMS: m/z 371 (M+1)⁺.
Retention time: 6.91 min

Example 20

2-(3,5-Difluoro-3'-methoxybiphenyl-4-ylamino)nicotinic acid

Obtained (31%) from intermediate 29 and 2-chloronicotinic acid following the experimental procedure described in example 1.
¹H NMR (200 MHz, DMSO-D₆) δ ppm: 3.8 (s, 3 H); 6.9 (dd, J=7.8, 4.7 Hz, 1 H); 7.0 (m, 1 H); 7.4 (m, 3 H); 7.5 (m, 2 H); 8.2 (m, 2 H); 9.5 (s, 1 H); 13.6 (s, 1 H)
LRMS: m/z 357 (M+1)⁺.
Retention time: 6.79 min

Example 21

Lithium 3-(3'-ethoxy-3-fluorobiphenyl-4-ylamino)isonicotinate

To a solution of intermediate 22 (0.12 g, 0.33 mmol) in THF (4 ml) at 0° C., was added 0.39M LiOH aqueous solution (0.02 g, 0.39 mmol) and the mixture was stirred at room temperature for 1 hour. The reaction mixture was purified by column chromatography eluting with the mixture of MeOH/DCM (from 30 to 50%) and the desired product was obtained as a white solid. Yield=76%.
¹H NMR (250 MHz, DMSO-D₆) δ ppm: 1.2 (t, 3H); 4.1 (q, 2H); 6.9 (m, 1H); 7.2 (m, 2H); 7.4 (t, 1H); 7.6 (m, 3H); 7.8 (d, 1H); 8.0 (d, 1H); 8.6 (s, 1H); 11.2 (bs, 1H).
LRMS: m/z 353 (M+1)⁺.
Retention time: 5.95 min

Example 22

Lithium 3-(3-fluoro-3'-methoxybiphenyl-4-ylamino)isonicotinate

Obtained (80%) from intermediate 23 following the experimental procedure described in example 21.
¹H NMR (250 MHz, DMSO-D₆) δ ppm: 3.8 (s, 3H); 6.9 (m, 1H); 7.3 (m, 3H); 7.5 (m, 3H); 7.8 (d, J=6.5 Hz, 1H); 8.0 (d, J=6.5 Hz, 1H) 8.5 (s, 1H); 11.1 (bs, 1H).
LRMS: m/z 339 (M+1)⁺.
Retention time: 5.43 min

Example 23

Lithium 3-(3'-methoxy-3-(trifluoromethoxy)biphenyl-4-ylamino)isonicotinate

Obtained (70%) from intermediate 24 following the experimental procedure described in example 21.
¹H NMR (250 MHz, DMSO-D₆): δ ppm 3.8 (s, 3H); 6.9 (m, 1H); 7.2 (m, 2H); 7.4 (t, 1H); 7.7 (m, 3H); 7.8 (d, 1H); 8.0 (d, 1H); 8.6 (s, 1H); 11.4 (bs, 1H).
LRMS: m/z 405 (M+1)⁺.
Retention time: 6.26 min

Example 24

Lithium 3-(3-fluoro-3'-(trifluoromethoxy)biphenyl-4-ylamino)isonicotinate

Obtained (39%) from intermediate 25 following the experimental procedure described in example 21.
¹H NMR (250 MHz, DMSO-D₆) δ ppm: 7.3 (m, 1H); 7.7 (m, 7H); 8.0 (m, 1H); 8.6 (s, 1H); 10.9 (bs, 1H).
LRMS: m/z 393 (M+1)⁺.
Retention time: 6.53 min

Example 25

2-(3'-Ethoxybiphenyl-4-ylamino)nicotinic acid

Obtained (25%) from intermediate 12 and 2-chloronicotinic acid following the experimental procedure described in example 1.
¹H NMR (200 MHz, CDCl₃) δ ppm: 1.5 (t, J=7.0 Hz, 3 H); 4.1 (q, J=7.0 Hz, 2 H); 6.8 (m, 1 H); 6.9 (m, 1 H); 7.2 (m, 2 H); 7.3 (m, 1 H); 7.6 (d, J=8.8 Hz, 2 H); 7.8 (d, J=8.8 Hz, 2 H); 8.3 (dd, J=7.8, 2.0 Hz, 1 H); 8.5 (dd, J=4.7, 2.0 Hz, 1 H); 10.1 (s, 1 H).
LRMS: m/z 335 (M+1)⁺.
Retention time: 6.97 min

Example 26

2-(5-Fluoro-2-methyl-3'-(trifluoromethoxy)biphenyl-4-ylamino)nicotinic acid

Obtained (42%) from intermediate 27 and 2-chloronicotinic acid following the experimental procedure described in example 1.

$^1$H NMR (200 MHz, DMSO-D$_6$): δ ppm 2.3 (s, 3 H); 7.0 (dd, J=7.8, 4.7 Hz, 1 H); 7.2 (d, J=12.1 Hz, 1 H); 7.4 (m, J=1.0 Hz, 3 H); 7.6 (d, J=9.0 Hz, 1 H); 8.3 (dd, J=7.4, 2.0 Hz, 1 H); 8.5 (m, 2 H); 10.7 (d, J=2.7 Hz, 1 H).

LRMS: m/z 407 (M+1)$^+$.
Retention time: 7.63 min

Example 27

2-(2',3-Difluoro-5'-isopropoxybiphenyl-4-ylamino)nicotinic acid

Obtained (57%) from intermediate 28 and 2-chloronicotinic acid following the experimental procedure described in example 1.

$^1$H NMR (200 MHz, DMSO-D$_6$): δ ppm 1.3 (d, J=6.2 Hz, 6 H); 4.7 (m, 1 H); 7.0 (m, 3 H); 7.2 (m, 1 H); 7.5 (m, 2 H); 8.3 (dd, J=7.8, 2.0 Hz, 1 H); 8.5 (dd, J=4.7, 2.0 Hz, 1 H); 8.7 (t, J=8.8 Hz, 1 H); 10.9 (d, J=2.7 Hz, 1 H).

LRMS: m/z 385 (M+1)$^+$.
Retention time: 7.51 min

Example 28

2-(3-Fluoro-3'-methoxybiphenyl-4-ylamino)-5-methylnicotinic acid

Obtained (13%) from intermediate 4 and intermediate 32 following the experimental procedure described in example 1.

LRMS: m/z 353 (M+1)$^+$.
Retention time: 7.00 min
$^1$H NMR (200 MHz, CD$_3$OD): δ ppm 2.2 (s, 3 H); 3.8 (s, 3 H); 6.8 (m, J=8.2, 2.3 Hz, 1 H); 7.1 (m, 2 H); 7.3 (m, 3 H); 8.1 (m, 2 H); 8.5 (t, J=8.6 Hz, 1 H).

Example 29

2-(3,5-Difluoro-3'hydroxybiphenyl-4-ylamino)nicotinic acid

Obtained (46%) from intermediate 21 and 3-(4,4,5,5-tetramethyl-1,3,2-dioxaborolan-2-yl)phenol, following the experimental procedure described in example 18.

LRMS: m/z 343 (M+1)$^+$.
Retention time: 5.71 min
$^1$H NMR (200 MHz, DMSO-D$_6$): δ ppm 6.8 (dd, J=7.6, 4.9 Hz, 2 H); 7.1 (m, 2 H); 7.3 (t, J=7.8 Hz, 1 H); 7.4 (d, J=9.4 Hz, 2 H); 8.2 (m, 2 H); 10.2 (s, 1 H)

Example 30

5-Bromo-2-(3-fluoro-3'-methoxybiphenyl-4-ylamino)nicotinic acid

Obtained (34%) from intermediate 4 and 5-bromo-2-chloronicotinic acid, following the experimental procedure described in example 1.

LRMS: m/z 417-419 (M+1)$^+$.
Retention time: 7.71 min

Example 31

5-Bromo-2-(3,5-difluoro-3'-methoxybiphenyl-4-ylamino)nicotinic acid

Obtained (13%) from intermediate 29 and 5-bromo-2-chloronicotinic acid, following the experimental procedure described in example 1.

LRMS: m/z 435-437 (M+1)$^+$.
Retention time: 6.93 min
$^1$H NMR (200 MHz, DMSO-D$_6$): δ ppm 3.8 (s, 3 H); 7.0 (m, 1 H); 7.4 (m, 3 H) 7.6 (d, J=9.8 Hz, 2 H); 8.3 (d, J=2.7 Hz, 1 H); 8.4 (d, J=2.3 Hz, 1 H); 9.6 (s, 1 H).

Example 32

5-Bromo-2-(3-fluoro-3'-(trifluoromethoxy)biphenyl-4-ylamino)nicotinic acid

Obtained (27%) from intermediate 2 and 5-bromo-2-chloronicotinic acid, following the experimental procedure described in example 1.

LRMS: m/z 471-473 (M+1)$^+$.
Retention time: 8.04 min

Example 33

2-(3-Fluoro-3'-(trifluoromethoxy)biphenyl-4-ylamino)-5-methylnicotinic acid

To a solution of example 32 (0.1 g, 0.21 mmol), K$_3$PO$_4$ (204 mg, 0.96 mmol), methylboronic acid (20 mg, 0.33 mmol) and tricyclohexylphosphine (14 mg, 0.04 mmol) in toluene/water (2 ml/0.1 ml) under nitrogen atmosphere was added Pd(OAc)$_2$ (5 mg, 0.02 mmol). The mixture was heated to 100° C. overnight and then cooled to room temperature. The reaction mixture was concentrated and the residue redissolved in ethyl acetate and water. The organic layer was washed with water and brine, dried over magnesium sulphate, filtered and the solvent evaporated under vacuum. The residue obtained was purified by reverse-phase chromatography eluting with a gradient of water and AcN/MeOH (1/1) (from 0% to 70% of AcN/MeOH(1/1)). The desired product was obtained as a yellow solid.

Yield=28%.
LRMS: m/z 407 (M+1)$^+$.
Retention time: 7.80 min
$^1$H NMR (200 MHz, CD$_3$OD): δ ppm 2.2 (s, 3 H); 7.1 (d, J=7.5 Hz, 1 H); 7.5 (m, 5 H); 8.1 (d, J=11.4 Hz, 2 H); 8.6 (t, J=8.4 Hz, 1 H).

Example 34

5-Cyclopropyl-2-(3-fluoro-3'-methoxybiphenyl-4-ylamino)nicotinic acid

Obtained (10%) from example 30 and cyclopropylboronic acid, following the experimental procedure described in example 33.

LRMS: m/z 379 (M+1)$^+$.
Retention time: 7.59 min
$^1$H NMR (200 MHz, DMSO-D$_6$): δ ppm 0.7 (m, 2 H); 1.0 (m, 2 H); 2.0 (m, 1 H); 3.8 (s, 3 H); 6.9 (m, 1 H); 7.3 (m, 3 H);

7.6 (m, 2 H); 8.0 (d, J=2.5 Hz, 1 H); 8.3 (d, J=2.5 Hz, 1 H); 8.7 (t, J=8.8 Hz, 1 H); 10.7 (d, J=2.0 Hz, 1 H).

Example 35

2-(3,5-Difluoro-3'-methoxybiphenyl-4-ylamino)-5-methylnicotinic acid

Obtained (10%) from example 31 and methylboronic acid, following the experimental procedure described in example 33.
LRMS: m/z 370 (M+1)$^+$.
Retention time: 6.57 min
$^1$H NMR (400 MHz, DMSO-D$_6$): δ ppm 2.2 (s, 3 H); 3.8 (s, 3H, 7.0 (dd, J=7.8, 1.7 Hz, 1 H); 7.4 (m, 3 H); 7.5 (d, J=9.4 Hz, 2 H); 8.1 (dd, J=20.2, 1.7 Hz, 2 H); 9.3 (s, 1 H); 13.6 (s, 1 H).

Example 36

2-(3'-Ethoxy-5-fluoro-2-methylbiphenyl-4-ylamino)nicotinic acid

Obtained (67%) from intermediate 26 and 2-chloronicotinic acid, following the experimental procedure described in example 1.
LRMS: m/z 367
Retention time: 7.08 min
$^1$H NMR (200 MHz, DMSO-D$_6$) δ ppm: 1.3 (t, J=6.8 Hz, 3 H); 2.2 (s, 3 H); 4.0 (q, J=6.8 Hz, 2 H); 6.9 (m, 4 H); 7.1 (d, J=12.1 Hz, 1 H); 7.3 (t, J=7.8 Hz, 1 H); 8.3 (dd, J=7.8, 2.0 Hz, 1 H); 8.4 (m, 2 H); 10.6 (d, J=2.3 Hz, 1 H).

Example 37

2-(5-Fluoro-3'-methoxy-2-methylbiphenyl-4-ylamino)nicotinic acid

Obtained (73%) from intermediate 30 and 2-chloronicotinic acid, following the experimental procedure described in example 1.
LRMS: m/z 353
Retention time: 6.75 min
$^1$H NMR (200 MHz, DMSO-D$_6$): δ ppm 2.2 (s, 3 H); 3.8 (s, 3 H); 6.9 (m, 4 H); 7.1 (d, J=12.1 Hz, 1 H); 7.3 (t, J=7.8 Hz, 1 H); 8.4 (m, 3 H); 10.6 (d, J=2.3 Hz, 1 H).

Example 38

2-(3'-ethoxy-3,5-difluorobiphenyl-4-ylamino)-5-methylnicotinic acid

Obtained (6%) from intermediate 34 and methylboronic acid, following the experimental procedure described in example 33.
LRMS: m/z 385 (M+1)$^+$.
Retention time: 7.06 min
$^1$H NMR (200 MHz, DMSO-D$_6$) δ ppm 1.4 (t, J=6.8 Hz, 3 H) 2.2 (s, 3 H) 4.1 (d, J=6.8 Hz, 2 H) 7.0 (d, J=1.6 Hz, 1 H) 7.4 (m, 5 H) 8.1 (d, J=7.0 Hz, 2 H) 9.4 (s, 1 H).

Example 39

5-cyclopropyl-2-(3'-ethoxy-3,5-difluorobiphenyl-4-ylamino)nicotinic acid

Obtained (14%) from intermediate 34 and cyclopropylboronic acid, following the experimental procedure described in example 33.
LRMS: m/z 411 (M+1)$^+$.
Retention time: 7.33 min
$^1$H NMR (200 MHz, DMSO-D$_6$) δ ppm 0.6 (m, 2 H) 0.9 (m, 2 H) 1.4 (t, J=6.9 Hz, 3 H) 1.9 (m, 1 H) 4.1 (q, J=6.9 Hz, 2 H) 7.0 (m, 1 H) 7.4 (m, 5 H) 7.9 (d, J=2.5 Hz, 1 H) 8.1 (d, J=2.5 Hz, 1 H) 9.4 (s, 1 H).

Example 40

2-(3,5-difluoro-3'-methoxybiphenyl-4-ylamino)-5-ethylnicotinic acid

To a solution of example 31 (200 mg, 0.46 mmol) and tributyl(vinyl)stannane (209 mg, 0.66 mmol) in DMF (8 ml) under nitrogen atmosphere was added Pd(PPh$_3$)$_4$ (37 mg, 0.07 mmol). The mixture was heated to 100° C. overnight and then cooled to room temperature. The reaction mixture was concentrated and the residue redissolved in ethyl acetate and water. The organic layer was washed with water and brine, dried over magnesium sulphate, filtered and the solvent evaporated under vacuum. The residue obtained was purified by flash chromatography eluting with Hexane/AcOEt (from 1/0 to 1/1). The solid obtained was redissolved in EtOH (10 ml) and Pd/C (46 mg, 0.04 mmol) was added and the reaction mixture stirred under hydrogen atmosphere overnight. The crude was filtered over celite and evaporated. The residue obtained was purified by reverse-phase chromatography eluting with a gradient of water and AcN/MeOH (1/1) (from 0% to 70% of AcN/MeOH(1/1)). The desired product was obtained as a yellow solid. Yield=23%.
LRMS: m/z 385 (M+1)$^+$.
Retention time: 7.01 min
$^1$H NMR (200 MHz, DMSO-D$_6$) δ ppm 1.2 (t, J=7.4 Hz, 3 H) 3.8 (m, 3 H) 7.0 (m, J=8.2 Hz, 1 H) 7.3 (m, 3 H) 7.5 (d, J=9.4 Hz, 2 H) 8.1 (m, 2 H) 9.6 (s, 1 H).

Example 41

5-bromo-2-(3'-ethoxy-2,5-difluorobiphenyl-4-ylamino)nicotinic acid

Obtained (70%) from intermediate 7 and 5-bromo-2-chloronicotinic acid following the experimental procedure described in intermediate 34.
LRMS: m/z 447, 449 (M+1)$^+$.
Retention time: 7.91 min
$^1$H NMR (200 MHz, DMSO-D$_6$) δ ppm 1.4 (t, J=6.9 Hz, 3 H) 4.1 (d, J=6.9 Hz, 2 H) 7.0 (m, 3 H) 7.4 (t, J=7.6 Hz, 1 H) 7.5 (dd, J=11.9, 7.6 Hz, 1 H) 8.4 (d, J=2.0 Hz, 1 H) 8.6 (m, 2 H) 10.9 (s, 1 H).

Example 42

5-cyclopropyl-2-(3'-ethoxy-2,5-difluorobiphenyl-4-ylamino)nicotinic acid

Obtained (26%) from example 41 and cyclopropylboronic acid, following the experimental procedure described in example 33.
LRMS: m/z 411 (M+1)$^+$.
Retention time: 6.71 min
$^1$H NMR (200 MHz, DMSO-D$_6$) δ ppm 0.7 (m, 2 H) 1.0 (m, 2 H) 1.4 (t, J=7.0 Hz, 3 H) 2.0 (m, 1 H) 4.1 (q, J=7.0 Hz, 2 H) 6.9 (m, 1 H) 7.1 (m, J=10.5 Hz, 2 H) 7.4 (t, J=8.0 Hz, 1 H) 7.5 (dd, J=12.1, 7.4 Hz, 1 H) 8.0 (d, J=2.3 Hz, 1 H) 8.4 (d, J=2.3 Hz, 1 H) 8.7 (dd, J=14.1, 7.0 Hz, 1 H) 10.9 (s, 1 H).

Example 43

2-(5-fluoro-3'-methoxy-2-methylbiphenyl-4-ylamino)-5-methylnicotinic acid

Obtained (20%) from intermediate 35 and methylboronic acid, following the experimental procedure described in example 33.
LRMS: m/z 367 (M+1)+.
Retention time: 7.35 min
$^1$H NMR (200 MHz, DMSO-D$_6$) δ ppm 2.2 (2s, 6 H) 3.8 (s, 3 H) 6.9 (m, 3 H) 7.1 (d, J=12.5 Hz, 1 H) 7.4 (m, 1 H) 8.1 (d, J=2.3 Hz, 1 H) 8.3 (d, J=2.3 Hz, 1 H) 8.5 (d, J=8.6 Hz, 1 H) 10.9 (s, 1 H).

Example 44

5-cyclopropyl-2-(5-fluoro-3'-methoxy-2-methylbiphenyl-4-ylamino)nicotinic acid

Obtained (6%) from intermediate 35 and cyclopropylboronic acid, following the experimental procedure described in example 33.
LRMS: m/z 393 (M+1)+.
Retention time: 7.62 min
$^1$H NMR (200 MHz, DMSO-D$_6$) δ ppm 0.7 (m, 2 H) 0.9 (m, 2 H) 1.9 (m, 1 H) 2.2 (s, 3 H) 3.8 (s, 3 H) 6.9 (m, 3 H) 7.1 (d, J=12.5 Hz, 1 H) 7.4 (t, J=7.8 Hz, 1 H) 7.9 (d, J=2.3 Hz, 1 H) 8.3 (d, J=2.3 Hz, 1 H) 8.5 (d, J=8.2 Hz, 1 H) 10.6 (s, 1 H).

Example 45

2-(2',3,5-trifluoro-3'-methoxybiphenyl-4-ylamino)nicotinic acid

Obtained (73%) from intermediate 21 and (2-fluoro-3-methoxyphenyl)boronic acid, following the experimental procedure described in example 18.
LRMS: m/z 375 (M+1)+.
Retention time: 6.50 min
$^1$H NMR (200 MHz, DMSO-D$_6$) δ ppm 3.9 (s, 3 H) 6.9 (dd, J=7.8, 4.7 Hz, 1 H) 7.2 (m, 3 H) 7.4 (d, J=8.2 Hz, 2 H) 8.2 (m, 2 H) 9.6 (s, 1 H).

Example 46

2-(2'-chloro-3,5-difluorobiphenyl-4-ylamino)nicotinic acid

Obtained (73%) from intermediate 21 and 2-chlorophenylboronic acid, following the experimental procedure described in example 18.
LRMS: m/z 361 (M+1)+.
Retention time: 6.75 min
$^1$H NMR (200 MHz, DMSO-D$_6$) δ ppm 6.9 (dd, J=7.8, 4.7 Hz, 1 H) 7.3 (d, J=8.6 Hz, 2 H) 7.5 (m, 4 H) 8.3 (m, 2 H) 9.6 (s, 1 H).

Example 47

2-(3'-cyclopropoxy-3,5-difluorobiphenyl-4-ylamino)nicotinic acid

Obtained (53%) from intermediate 21 and intermediate 37, following the experimental procedure described in example 18.
LRMS: m/z 383 (M+1)+.
Retention time: 7.06 min
$^1$H NMR (400 MHz, DMSO-D$_6$) δ ppm 0.7 (m, 2 H) 0.8 (m, 2 H) 4.0 (m, 1 H) 6.9 (dd, J=7.4, 4.7 Hz, 1 H) 7.1 (m, 1 H) 7.4 (m, 3 H) 7.5 (d, J=9.4 Hz, 2 H) 8.2 (m, 2 H) 9.5 (s, 1 H) 13.6 (s, 1 H).

Example 48

2-(3,5-difluoro-2-methylbiphenyl-4-ylamino)nicotinic acid

Obtained (33%) from 2-chloronicotinic acid and intermediate 38 following the experimental procedure described in example 1.
LRMS: m/z 341 (M+1)+.
Retention time: 7.02 min
$^1$H NMR (200 MHz, DMSO-D$_6$) δ ppm 2.1 (s, 3 H) 6.9 (dd, J=7.8, 4.7 Hz, 1 H) 7.1 (dd, J=10.5, 2.0 Hz, 1 H) 7.4 (m, 5 H) 8.2 (m, 2 H) 9.5 (s, 1 H).

Example 49

5-cyclopropyl-2-(2,5-difluoro-3'-methoxybiphenyl-4-ylamino)nicotinic acid

Obtained (7%) from intermediate 39 and cyclopropylboronic acid, following the experimental procedure described in example 33.
LRMS: m/z 397 (M+1)+.
Retention time: 7.77 min
$^1$H NMR (400 MHz, DMSO-D$_6$) δ ppm 0.7 (d, J=5.2 Hz, 2 H) 1.0 (d, J=8.3 Hz, 2 H) 2.0 (m, 1 H) 3.8 (s, 3 H) 7.0 (d, J=7.2 Hz, 1 H) 7.1 (m, 2 H) 7.4 (t, J=7.9 Hz, 1 H) 7.5 (dd, J=12.1, 7.4 Hz, 1 H) 8.0 (s, 1 H) 8.4 (s, 1 H) 8.7 (dd, J=13.7, 7.0 Hz, 1 H) 10.8 (s, 1 H) 13.9 (s, 1 H).

Example 50

2-(3'-cyclopropoxy-3,5-difluorobiphenyl-4-ylamino)-5-cyclopropylnicotinic acid

Obtained (30%) from intermediate 42 and intermediate 37, following the experimental procedure described in example 18.
LRMS: m/z 423 (M+1)+.
Retention time: 7.44 min
$^1$H NMR (200 MHz, DMSO-D$_6$) δ ppm 0.8 (m, 8 H) 1.9 (m, 1 H) 4.0 (m, 1 H) 7.1 (m, 1 H) 7.4 (m, 5 H) 7.9 (d, J=2.3 Hz, 1 H) 8.1 (d, J=2.3 Hz, 1 H) 9.3 (s, 1 H) 13.6 (s, 1 H).

Example 51

5-chloro-2-(3,5-difluoro-3'-methoxybiphenyl-4-ylamino)nicotinic acid

Obtained (19%) from intermediate 29 and 2,5-dichloronicotinic acid following the experimental procedure described in intermediate 34.
LRMS: m/z 391 (M+1)+.
Retention time: 7.28 min ¹H NMR (400 MHz, DMSO-D₆) δ ppm 3.8 (s, 3 H) 7.0 (dd, J=7.8, 1.6 Hz, 1 H) 7.4 (m, 3 H) 7.6 (2s, 2 H) 8.2 (d, J=2.5 Hz, 1 H) 8.3 (d, J=2.5 Hz, 1 H) 9.5 (s, 1 H).

Example 52

5-cyclopropyl-2-(3,5-difluoro-3'-(trifluoromethoxy)biphenyl-4-ylamino)nicotinic acid Obtained (48%) from intermediate 42 and 3-(trifluoromethoxy)phenylboronic acid, following the experimental procedure described in example 18.
LRMS: m/z 451 (M+1)⁺.
Retention time: 7.48 min
¹H NMR (400 MHz, DMSO-D₆) δ ppm 0.6 (m, 2 H) 0.9 (m, 2 H) 1.9 (m, 1 H) 7.4 (m, 1 H) 7.6 (m, 3 H) 7.8 (s, 1 H) 7.8 (dd, J=7.4, 1.2 Hz, 1 H) 7.9 (d, J=2.3 Hz, 1 H) 8.1 (d, J=2.7 Hz, 1 H) 9.4 (s, 1 H) 13.6 (s, 1 H).

Example 53

2-(2,3,5-trifluoro-3'-methoxybiphenyl-4-ylamino)nicotinic acid

Obtained (6%) from intermediate 43 and 2-chloronicotinic acid following the experimental procedure described in intermediate 34.
LRMS: m/z 375 (M+1)⁺.
Retention time: 6.79 min
¹H NMR (400 MHz, DMSO-D₆) δ ppm 3.8 (s, 3 H) 6.7 (m, 1 H) 7.1 (m, 3 H) 7.4 (m, 2 H) 8.0 (s, 1 H) 8.2 (m, 1 H) 11.8 (s, 1 H)

Example 54

2-(2'-chloro-3,5-difluorobiphenyl-4-ylamino)-5-cyclopropylnicotinic acid

Obtained (38%) from intermediate 42 and 2-chlorophenylboronic acid, following the experimental procedure described in example 18.
LRMS: m/z 401 (M+1)⁺.
Retention time: 7.27 min
¹H NMR (400 MHz, DMSO-D₆) δ ppm 0.7 (m, 2 H) 0.9 (m, 2 H) 1.9 (m, 1 H) 7.3 (2s, 2 H) 7.5 (m, 3 H) 7.6 (dd, J=5.8, 3.6 Hz, 1 H) 7.9 (d, J=2.6 Hz, 1 H) 8.1 (d, J=2.6 Hz, 1 H) 9.4 (s, 1 H) 13.6 (s, 1 H)

Example 55

2-(3,5-difluoro-3'-methoxy-2-methylbiphenyl-4-ylamino)nicotinic acid

Obtained (68%) from intermediate 45 and 3-methoxyphenylboronic acid, following the experimental procedure described in example 18.
LRMS: m/z 371 (M+1)⁺.
Retention time: 6.76 min
¹H NMR (200 MHz, DMSO-D₆) δ ppm 2.1 (d, J=2.0 Hz, 3 H) 3.8 (s, 3 H) 6.8 (dd, J=7.6, 4.9 Hz, 1 H) 7.0 (m, 4 H) 7.4 (t, J=8.2 Hz, 1 H) 8.2 (m, 2 H) 9.7 (s, 1 H)

Example 56

2-(3,5-difluoro-2-methyl-3'-(trifluoromethoxy)biphenyl-4-ylamino)nicotinic acid

Obtained (63%) from intermediate 45 and 3-(trifluoromethoxy)phenylboronic acid, following the experimental procedure described in example 18.
LRMS: m/z 425 (M+1)⁺.
Retention time: 7.31 min
¹H NMR (200 MHz, DMSO-D₆) δ ppm 2.1 (d, J=2.0 Hz, 3 H) 6.9 (dd, J=7.8, 5.1 Hz, 1 H) 7.1 (dd, J=10.3, 1.8 Hz, 1 H) 7.5 (m, 3 H) 7.6 (d, J=7.8 Hz, 1 H) 8.2 (m, 2 H) 9.6 (s, 1 H)

Example 57

2-(2'-chloro-3,5-difluoro-2-methylbiphenyl-4-ylamino)nicotinic acid

Obtained (63%) from intermediate 45 and 2-chlorophenylboronic acid, following the experimental procedure described in example 18.
LRMS: m/z 375 (M+1)⁺.
Retention time: 6.99 min
¹H NMR (200 MHz, DMSO-D₆) δ ppm 2.0 (s, 3 H) 6.9 (dd, J=7.6, 4.9 Hz, 1 H) 7.0 (m, 1 H) 7.4 (m, 3 H) 7.6 (dd, J=5.9, 3.1 Hz, 1 H) 8.3 (m, 2 H) 9.6 (s, 1 H)

Example 58

5-chloro-2-(3,5-difluorobiphenyl-4-ylamino)nicotinic acid

Obtained (23%) from intermediate 46 and phenylboronic acid, following the experimental procedure described in example 18.
LRMS: m/z 361 (M+1)⁺.
Retention time: 7.37 min
¹H NMR (400 MHz, DMSO-D₆) δ ppm 7.4 (t, J=7.4 Hz, 1 H) 7.5 (m, 4 H) 7.8 (d, J=7.4 Hz, 2 H) 8.2 (d, J=2.7 Hz, 1 H) 8.3 (d, J=2.7 Hz, 1 H) 9.5 (s, 1 H)

Example 59

5-chloro-2-(2'-chloro-3,5-difluorobiphenyl-4-ylamino)nicotinic acid

Obtained (15%) from intermediate 46 and 2-chlorophenylboronic acid, following the experimental procedure described in example 18.
LRMS: m/z 395 (M+1)⁺.
Retention time: 7.48 min
¹H NMR (400 MHz, DMSO-D₆) δ ppm 7.3 (d, J=8.7 Hz, 2 H) 7.5 (m, 3 H) 7.6 (m, 1 H) 8.2 (d, J=2.5 Hz, 1 H) 8.3 (d, J=2.5 Hz, 1 H) 9.6 (s, 1 H) 14.0 (s, 1 H)

Example 60

2-(2,3,5,6-tetrafluoro-3'-methoxybiphenyl-4-ylamino)nicotinic acid

Obtained (3%) from intermediate 47 and 2-chloronicotinic acid following the experimental procedure described in intermediate 34.
LRMS: m/z 393 (M+1)⁺.
Retention time: 6.97 min
¹H NMR (200 MHz, DMSO-D₆) δ ppm 3.8 (s, 3 H) 6.9 (dd, J=7.6, 4.9 Hz, 1 H) 7.1 (m, 3 H) 7.5 (t, J=8.2 Hz, 1 H) 8.3 (m, 2 H) 10.2 (s, 1 H)

Example 61

2-(3,5-difluoro-2'-methylbiphenyl-4-ylamino)nicotinic acid

Obtained (63%) from intermediate 21 and o-tolylboronic acid, following the experimental procedure described in example 18.

LRMS: m/z 341 (M+1)⁺.

Retention time: 6.91 min

¹H NMR (400 MHz, DMSO-D₆) δ ppm 2.3 (s, 3 H) 6.9 (dd, J=7.6, 4.9 Hz, 1 H) 7.2 (d, J=8.6 Hz, 2 H) 7.3 (m, 4 H) 8.2 (dd, J=7.6, 1.9 Hz, 1 H) 8.3 (dd, J=4.7, 1.9 Hz, 1 H) 9.5 (s, 1 H)

Example 62

3-(3'-cyclopropoxy-3-fluorobiphenyl-4-ylamino) isonicotinic acid

To a solution of intermediate 51 (0.13 g, 0.34 mmol) in THF (5 ml) at 0° C., was added 0.39M LiOH aqueous solution (0.02 g, 0.41 mmol) and the mixture was stirred at room temperature overnight. THF was evaporated and the residue diluted with water. The pH was adjusted to 4-5 by adding a 5N solution of HCl and the solid formed was filtered and washed with DCM. The desired product was obtained as a yellow solid. Yield=62%.

LRMS: m/z 365 (M+1)⁺.

Retention time: 6.42 min

¹H NMR (400 MHz, DMSO-D₆) δ ppm 0.7 (s, 2 H) 0.8 (m, 2 H) 4.0 (m, 1 H) 7.1 (m, 1 H) 7.4 (m, 3 H) 7.6 (m, 4 H) 8.1 (d, J=5.1 Hz, 1 H) 8.5 (s, 1 H) 9.3 (s, 1 H).

TABLE 1

| Example | Structure |
|---|---|
| 1 | |
| 2 | |
| 3 | |
| 4 | 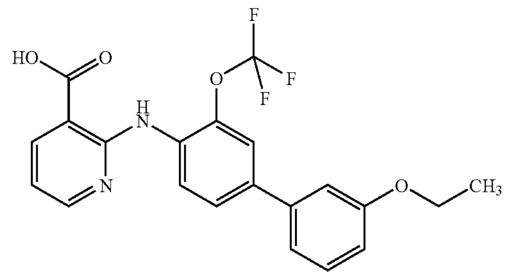 |
| 5 | 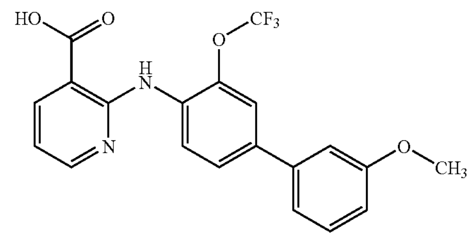 |
| 6 | 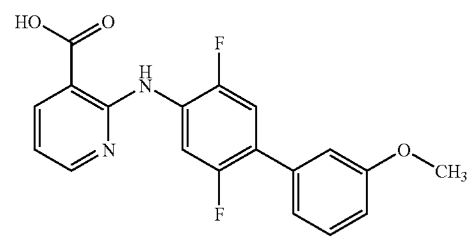 |
| 7 | 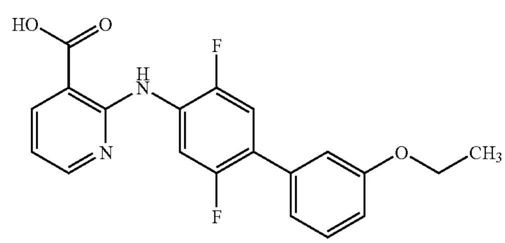 |
| 8 | 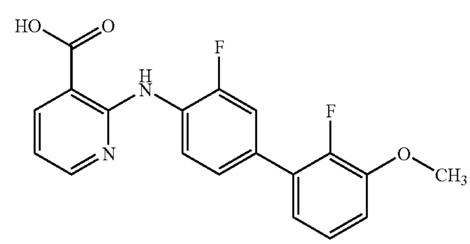 |
| 9 | 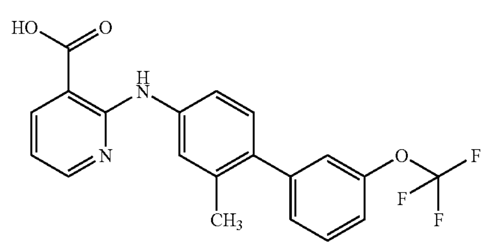 |

TABLE 1-continued

| Example | Structure |
|---|---|
| 10 | 2-[(2-chloro-3'-(trifluoromethoxy)-[1,1'-biphenyl]-4-yl)amino]nicotinic acid |
| 11 | 2-[(2-chloro-3'-ethoxy-[1,1'-biphenyl]-4-yl)amino]nicotinic acid |
| 12 | 2-[(2-methyl-3'-(trifluoromethoxy)-[1,1'-biphenyl]-4-yl)amino]nicotinic acid |
| 13 | 2-[(2-chloro-3'-methoxy-[1,1'-biphenyl]-4-yl)amino]nicotinic acid |
| 14 | 2-[(3'-(difluoromethoxy)-2-fluoro-[1,1'-biphenyl]-4-yl)amino]nicotinic acid |
| 15 | 2-[(3'-cyclobutoxy-2-fluoro-[1,1'-biphenyl]-4-yl)amino]nicotinic acid |
| 16 | 2-[(2-fluoro-3'-(2,2,2-trifluoroethoxy)-[1,1'-biphenyl]-4-yl)amino]nicotinic acid |
| 17 | 2-[(3'-cyclobutoxy-2,6-difluoro-[1,1'-biphenyl]-4-yl)amino]nicotinic acid |
| 18 | 2-[(2,6-difluoro-3'-(trifluoromethoxy)-[1,1'-biphenyl]-4-yl)amino]nicotinic acid |
| 19 | 2-[(3'-ethoxy-2,6-difluoro-[1,1'-biphenyl]-4-yl)amino]nicotinic acid |
| 20 | 2-[(2,6-difluoro-3'-methoxy-[1,1'-biphenyl]-4-yl)amino]nicotinic acid |
| 21 | lithium 3-[(3'-ethoxy-2-fluoro-[1,1'-biphenyl]-4-yl)amino]isonicotinate |

TABLE 1-continued

| Example | Structure |
|---|---|
| 22 | (Li carboxylate pyridine)-NH-(2-fluoro-4-(3-methoxyphenyl)phenyl) |
| 23 | (Li carboxylate pyridine)-NH-(2-trifluoromethoxy-4-(3-methoxyphenyl)phenyl) |
| 24 | (Li carboxylate pyridine)-NH-(2-fluoro-4-(3-trifluoromethoxyphenyl)phenyl) |
| 25 | (HOOC pyridine)-NH-(4-(3-ethoxyphenyl)phenyl) |
| 26 | (HOOC pyridine)-NH-(2-fluoro-5-methyl-4-(3-trifluoromethoxyphenyl)phenyl) |
| 27 | (HOOC pyridine)-NH-(2-fluoro-4-(2-fluoro-5-isopropoxyphenyl)phenyl) |
| 28 | (HOOC-5-methylpyridine)-NH-(2-fluoro-4-(3-methoxyphenyl)phenyl) |
| 29 | (HOOC pyridine)-NH-(2,6-difluoro-4-(3-hydroxyphenyl)phenyl) |
| 30 | (HOOC-5-bromopyridine)-NH-(2-fluoro-4-(3-methoxyphenyl)phenyl) |
| 31 | (HOOC-5-bromopyridine)-NH-(2,6-difluoro-4-(3-methoxyphenyl)phenyl) |
| 32 | (HOOC-5-bromopyridine)-NH-(2-fluoro-4-(3-trifluoromethoxyphenyl)phenyl) |
| 33 | (HOOC-5-methylpyridine)-NH-(2-fluoro-4-(3-trifluoromethoxyphenyl)phenyl) |

TABLE 1-continued
| Example | Structure |
|---|---|
| 34 | 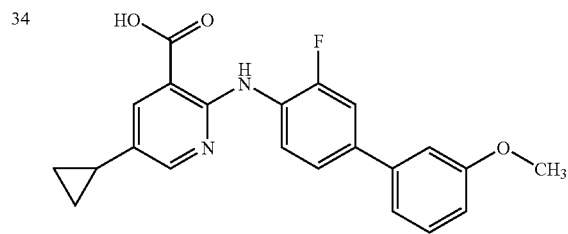 |
| 35 | 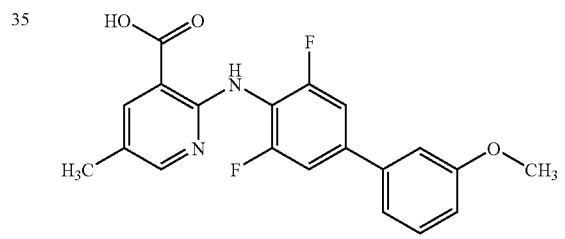 |
| 36 | 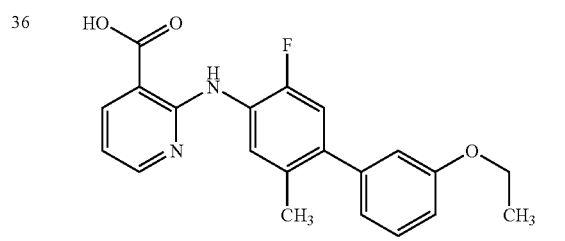 |
| 37 | 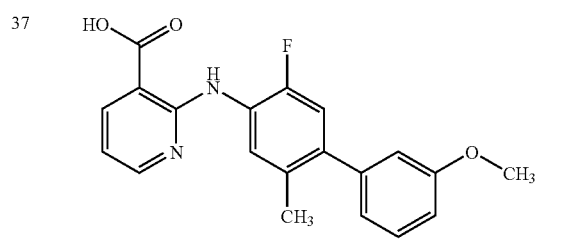 |
| 38 | 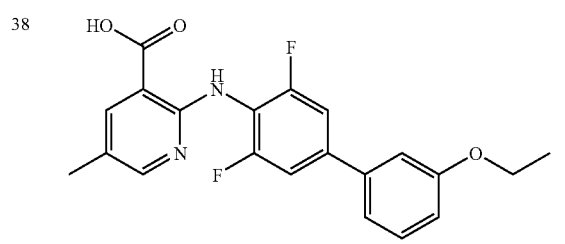 |
| 39 | 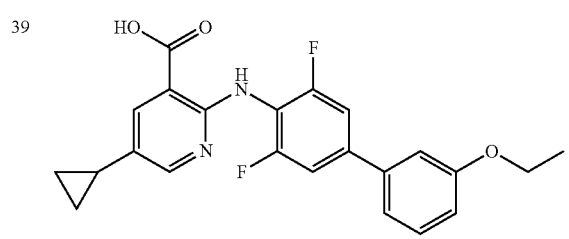 |
| 40 | 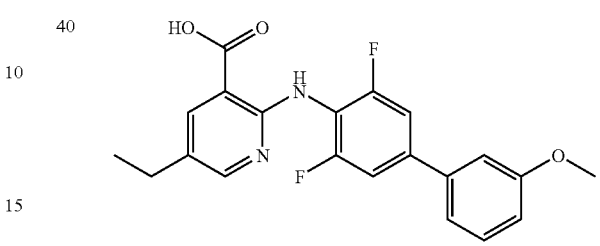 |
| 41 | 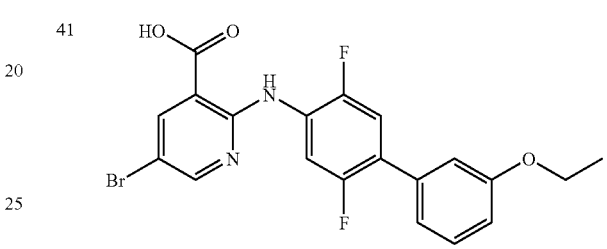 |
| 42 | 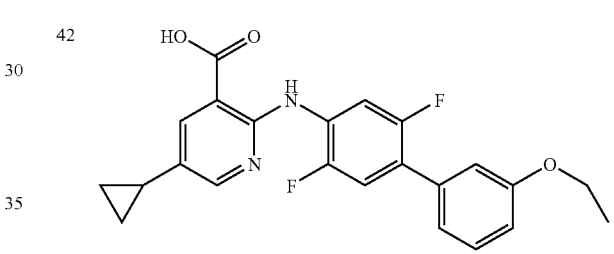 |
| 43 | 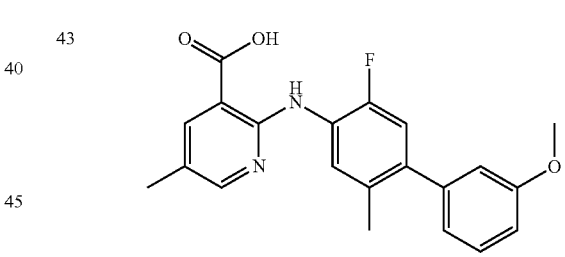 |
| 44 | 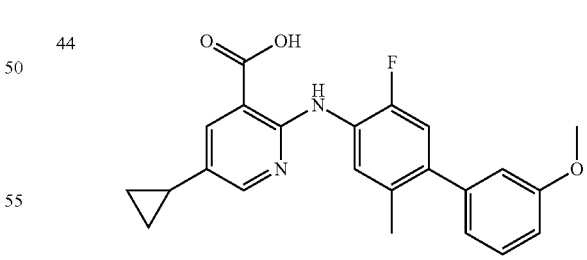 |
| 45 | 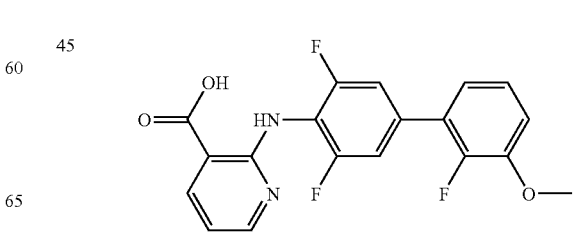 |

TABLE 1-continued

| Example | Structure |
|---|---|
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |
| 55 | (structure) |
| 56 | (structure) |
| 57 | (structure) |

TABLE 1-continued

| Example | Structure |
|---|---|
| 58 | 5-chloro-2-[(2,6-difluoro-4-phenylphenyl)amino]pyridine-3-carboxylic acid |
| 59 | 5-chloro-2-[(4-(2-chlorophenyl)-2,6-difluorophenyl)amino]pyridine-3-carboxylic acid |
| 60 | 2-[(2,3,5,6-tetrafluoro-3'-methoxy-[1,1'-biphenyl]-4-yl)amino]pyridine-3-carboxylic acid |
| 61 | 2-[(2,6-difluoro-2'-methyl-[1,1'-biphenyl]-4-yl)amino]pyridine-3-carboxylic acid |
| 62 | 3-[(3'-cyclopropoxy-3-fluoro-[1,1'-biphenyl]-4-yl)amino]isonicotinic acid |

Pharmacological Activity

Inhibition of Human DHODH Activity Assay

DHODH activity and its inhibition were studied using a chromogen reduction assay with DCIP (2,6-dichlorophenol-indophenol). The substrate oxidation (Dihydroorotate, L-DHO), as well as cosubstrate reduction (coenzyme Q, CoQ) is coupled to the chromogen reduction, hence enzymatic activity results in a loss of chromogen absorbance at 600 nm.

Enzyme extracts (8 μl, ~1.5 μg of human protein) were incubated in 96-well plates. The assay mixture (200 μl) contained 200 μM CoQD, 100 μM L-DHO, 120 μM DCIP in the assay buffer (100 mM HEPES pH 8.0, 150 mM NaCl, 10% Glicerol, 0.05% Triton X-100) and 2 μl of test compound. The compounds were dissolved in DMSO at a stock concentration of 1 mM, and tested at different concentrations varying from 10 μM to 1 pM to calculate an $IC_{50}$ (concentration of inhibitor required for 50% of inhibition).

The reaction was initiated by adding the enzyme and then incubated for 10 min at room temperature before measuring DCIP reduction by counting a decrease in absorbance at 600 nm using standard instrumentation (Spectramax).

All reactions were carried out in duplicate and graphs, determining $IC_{50}$ values for each compound, were plotted using the ABase software.

Table 2 shows the activities in human DHODH inhibition assay of some compounds of the present invention showing that these compounds are potent DHODH inhibitors.

TABLE 2

| Example | hDHODH $IC_{50}$ (nM) |
|---|---|
| 2 | 200 |
| 6 | 88 |
| 13 | 150 |
| 17 | 90 |
| 19 | 19 |
| 20 | 15 |
| 21 | 19 |
| 23 | 14 |
| 24 | 200 |
| 33 | 110 |
| 34 | 33 |
| 35 | 12 |
| 37 | 99 |
| 40 | 12 |
| 42 | 23 |
| 45 | 53 |
| 47 | 17 |
| 48 | 5 |
| 50 | 6 |
| 52 | 4 |
| 54 | 5 |
| 56 | 6 |
| 57 | 4 |
| 58 | 8 |
| 60 | 3 |
| 61 | 11 |

Functional Assay: Inhibition of Lymphocyte Proliferation

Peripheral blood mononuclear cells (PBMC) of healthy volunteers were prepared using Ficoll density centrifugation. Cells were seeded at $1 \times 10^5$ cells per well in 96 well flat bottom plates in RPMI 1640 supplemented with 5% fetal bovine serum, 2 mM L-glutamine and penicillin/streptomycin. Then, PBMC were activated with 1 μg/ml phytohaemagglutinin (PHA, Sigma) and incubated with a dilution series of different concentrations of test compounds for 3 days. After this period, cells were pulsed with 0.5 μCi per well of tritiated thymidine and incubated overnight. Next, the cultures are harvested on filter papers and counted with a B-counter. The $IC_{50}$ value for each compound was calculated from the dose response curves.

The compounds of the invention that have been tested using this Assay had an $IC_{50}$ of less than 10 μM. Preferred compounds of the invention had $IC_{50}$ of less than 4 μM, preferably lower than 2 μM, most preferably lower than 1 μM.

As shown by these results, the compounds of the invention effectively inhibit DHODH thereby inhibiting the proliferation of cells with high turnover, in particular lymphocytes.

The amino(iso)nicotinic acid derivatives of the invention are useful in the treatment or prevention of diseases known to be susceptible to improvement by treatment with inhibitor of the dihydroorotate dehydrogenase. Such diseases include but are not limited to rheumatoid arthritis, psoriatic arthritis, ankylosing spondilytis, multiple sclerosis, Wegener's granulomatosis, systemic lupus erythematosus, psoriasis and sarcoidosis.

Accordingly, the amino(iso)nicotinic acid derivatives of the invention and pharmaceutical compositions comprising such compound and/or salts thereof may be used in a method of treatment of disorders of the human or animal body which comprises administering to a subject requiring such treatment an effective amount of amino(iso)nicotinic acid derivative of the invention or a pharmaceutically acceptable salt thereof.

The amino(iso)nicotinic acid derivatives of the invention may also be combined with other active compounds in the treatment of diseases known to be susceptible to improvement by treatment with an inhibitor of the dihydroorotate dehydrogenase.

The combinations of the invention can optionally comprise one or more additional active substances which are known to be useful in the treatment of autoimmune diseases, immune and inflammatory diseases, destructive bone disorders, malignant neoplastic diseases, angiogenic-related disorders, viral diseases, and infectious diseases such as (a) Anti-TNF-alpha monoclonal antibodies such as Infliximab, Certolizumab pegol, Golimumab, Adalimumab and AME-527 from Applied Molecular Evolution, (b) Antimetabolite compounds such as Mizoribine, Cyclophosphamide and Azathiopirine, (c) Calcineurin (PP-2B) Inhibitors/INS Expression Inhibitors such as cyclosporine A, Tacrolimus and ISA-247 from Isotechnika, (d) Cyclooxygenase Inhibitors such as Aceclofenac, Diclofenac, Celecoxib, Rofecoxib, Etoricoxib, Valdecoxib, Lumiracoxib, Cimicoxib and LAS-34475 from Laboratorios Almirall, S.A., (e) TNF-alpha Antagonists such as Etanercept, Lenercept, Onercept and Pegsunercept, (f) NF-kappaB (NFKB) Activation Inhibitors such as Sulfasalazine and Iguratimod, (g) IL-1 Receptor Antagonists such as Anakinra and AMG-719 from Amgen, (h) Dihydrofolate Reductase (DHFR) Inhibitors such as Methrotexate, Aminopterin and CH-1504 from Chelsea, (i) Inhibitors of Inosine 5'-Monophosphate Dehydrogenase (IMPDH) such as Mizoribine, Ribavirin, Tiazofurin, Amitivir, Mycophenolate mofetil, Ribamidine and Merimepodib, (j) Glucocorticoids such as Prednisolone,Methylprednisolone,Dexamethasone, Cortisol, Hydrocortisone, Triamcinolone acetonide, Fluocinolone acetonide, Fluocinonide, Clocortolone pivalate, Hydrocortisone aceponate, Methylprednisolone suleptanate, Betamethasone butyrate propionate, Deltacortisone, Deltadehydrocortisone, Prednisone, Dexamethasone sodium phosphate, Triamcinolone, Betamethasone valerate, Betamethasone, Hydrocortisone sodium succinate, Prednisolone sodium phosphate, Hydrocortisone probutate and Difluprednate, (k) Anti-CD20 monoclonal antibodies such as Rituximab, Ofatumumab, Ocrelizumab and TRU-015 from Trubion Pharmaceuticals, (l)

B-targeted cell therapies such as BLYSS, BAFF, TACIK-Ig and APRIL, (m) p38 Inhibitors such as AMG-548 (from Amgen), ARRY-797 (from Array Biopharma), Chlormethiazole edisylate, Doramapimod, PS-540446 (from BMS), SB-203580, SB-242235, SB-235699, SB-281832, SB-681323, SB-856553 (all from GlaxoSmithKline), KC-706 (from Kemia), LEO-1606, LEO-15520 (all from Leo), SC-80036, SD-06 (all from Pfizer), RWJ-67657 (from R. W. Johnson), RO-3201195, RO-4402257 (all from Roche), AVE-9940 (from Aventis), SCIO-323, SCID-469 (all from Scios), TA-5493 (from Tanabe Seiyaku), and VX-745, VX-702 (all from Vertex) and the compounds claimed or described in Spanish patent applications numbers P200600396 and P200602174, (n) Jak3 Inhibitors such as CP690550 from Pfizer, (o) Syk inhibitors such as R-112, R-406 and R-788 all from Rigel, (p) MEK inhibitors such as ARRY-142886, ARRY-438162 (all from Array Biopharma), AZD-6244 (from AstraZeneca), PD-098059, PD-0325901 (all from Pfizer), (q) P2X7 receptor antagonist such as AZD-9056 from AstraZeneca, (r) 51 P1 agonists such as Fingolimod, CS-0777 from Sankyo and R-3477 from Actelion, (s) Anti-CD49 monoclonal antibodies such as Natalizumab, (t) Integrin Inhibitors such as Cilengitide, Firategrast, Valategrast hydrochloride, SB-273005, SB-683698 (all from Glaxo), HMR-1031 from Sanofi-Aventis, R-1295 from Roche, BMS-587101 from BMS and CDP-323 from UCB Celltech, (u) Anti-CD88 monoclonal antibodies such as Eculizumab and Pexelizumab, (v) IL-6 receptor antagonist such as CBP-1011 from InKine and C-326 from Amgen, (w) Anti IL-6 monoclonal antibodies such as Elsilimomab, CNTO-328 from Centocor and VX-30 from Vaccinex, (x) Anti-CD152 monoclonal antibodies such as Ipilimumab and Ticilimumab, (y) Fusion proteins comprising the extracellular domain of human cytotoxic T-lymphocyte-associated antigen 4 (CTLA-4) linked to portions of human immunoglobulin G1 such as Abatacept, (z) Agents useful in the treatment of bone disorders such as Bisphosphonates such as Tiludronate disodium, Clodronate disodium, Disodium pamidronate, Etidronate disodium, Xydiphone (K,Na salt), Alendronate sodium, Neridronate, Dimethyl-APD, Olpadronic acid sodium salt, Minodronic acid, Apomine, Ibandronate sodium hydrate and Risedronate sodium, (aa) VEGF Try kinase inhibitors such as Pegaptanib octasodium, Vatalanib succinate, Sorafenib, Vandetanib, Sunitinib malate, Cediranib, Pazopanib hydrochloride and AE-941 from AEterna Zentaris, (bb) Other compounds efficacious in autoimmune diseases such as Gold salts, hydroxycloroquinine, Penicilamine, K-832, SMP114 and AD452, (cc) Purine-Nucleoside phosphorylase inhibitors such as Forodesine hydrochloride, R-3421 from Albert Einstein College of Medicine, CI-972 and CI-1000 both from Pfizer, (dd) Anti-RANKL monoclonal antibodies such as Denosumab, (ee) Anti-CD25 monoclonal antibodies such as Inolimomab, Daclizimab, Basiliximab and LMB-2 from the US National Cancer Institute, (ff) Histone Deacetylase (HDAC) Inhibitors such as Divalproex sodium, Acetyldinaline, Depsipeptide, Sodium butyrate, Sodium phenylbutyrate, Vorinostat, MS-27-275 from Mitsui, Valproic acid, Pyroxamide, Tributyrin, PX-105684 from TopoTarget, MG-0103 from MethylGene, G2M-777 from TopoTarget and CG-781 from Celera and (gg) Anti colony-stimulating factor (GM-CSF) monoclonal antibodies such as KB-002 from KaloBios.

When amino(iso)nicotinic acid derivatives of the invention are used for the treatment of rheumatoid arthritis, psoriatic arthritis, ankylosing spondilytis, multiple sclerosis, Wegener's granulomatosis, systemic lupus erythematosus, psoriasis and sarcoidosis it may be advantageous to use them in combination with other active compounds known to be useful in the treatment of such diseases such as rheumatoid arthritis, psoriatic arthritis, ankylosing spondilytis, multiple sclerosis, Wegener's granulomatosis, systemic lupus erythematosus, psoriasis and sarcoidosis.

Particularly preferred actives to be combined with the amino(iso)nicotinic acid derivatives of the invention for treating or preventing rheumatoid arthritis, psoriatic arthritis, ankylosing spondilytis, multiple sclerosis, Wegener's granulomatosis, systemic lupus erythematosus, psoriasis or sarcoidosis are (a) Anti-TNF-alpha monoclonal antibodies such as Infliximab, Certolizumab pegol, Golimumab, Adalimumab and AME-527 from Applied Molecular Evolution, (b) TNF-alpha Antagonists such as Etanercept, Lenercept, Onercept and Pegsunercept, (c) Calcineurin (PP- 2B) Inhibitors/INS Expression Inhibitors such as cyclosporine A, Tacrolimus and ISA-247 from Isotechnika, (d) IL-1 Receptor Antagonists such as Anakinra and AMG-719 from Amgen, (e) Anti-CD20 monoclonal antibodies such as Rituximab, Ofatumumab, Ocrelizumab and TRU-015 from Trubion Pharmaceuticals, (f) p38 Inhibitors such as AMG-548 (from Amgen), ARRY-797 (from Array Biopharma), Chlormethiazole edisylate, Doramapimod, PS-540446 (from BMS), SB-203580, SB-242235, SB-235699, SB-281832, SB-681323, SB-856553 (all from GlaxoSmithKline), KC-706 (from Kemia), LEO-1606, LEO-15520 (all from Leo), SC-80036, SD-06 (all from Pfizer), RWJ-67657 (from R. W. Johnson), RO-3201195, RO-4402257 (all from Roche), AVE-9940 (from Aventis), SCIO-323, SCID-469 (all from Scios), TA-5493 (from Tanabe Seiyaku), and VX-745, VX-702 (all from Vertex) and the compounds claimed or described in Spanish patent applications numbers P200600396 and P200602174, (g) NF-kappaB (NFKB) Activation Inhibitors such as Sulfasalazine and Iguratimod and (h) Dihydrofolate Reductase (DHFR) Inhibitors such as Methrotexate, Aminopterin and CH-1504 from Chelsea The combinations of the invention may be used in the treatment of disorders which are susceptible to amelioration by inhibition of the dihydroorotate dehydrogenase. Thus, the present application encompasses methods of treatment of these disorders, as well as the use of the combinations of the invention in the manufacture of a medicament for the treatment of these disorders.

Preferred examples of such disorders are rheumatoid arthritis, psoriatic arthritis, ankylosing spondilytis, multiple sclerosis, Wegener's granulomatosis, systemic lupus erythematosus, psoriasis and sarcoidosis, more preferably rheumatoid arthritis, psoriatic arthritis and psoriasis and most preferably rheumatoid arthritis.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the inhibitor of the dihydroorotate dehydrogenase of the invention, and the other optional active compounds may be administered together in the same pharmaceutical composition or in different compositions intended for separate, simultaneous, concomitant or sequential administration by the same or a different route.

One execution of the present invention consists of a kit of parts comprising an inhibitor of the dihydroorotate dehydrogenase of the invention together with instructions for simultaneous, concurrent, separate or sequential use in combination with another active compound useful in the treatment of rheumatoid arthritis, psoriatic arthritis, ankylosing spondilytis, multiple sclerosis, Wegener's granulomatosis, systemic lupus erythematosus, psoriasis and sarcoidosis.

Another execution of the present invention consists of a package comprising an inhibitor of the dihydroorotate dehydrogenase of formula (I) and another active compound useful in the treatment of rheumatoid arthritis, psoriatic arthritis, ankylosing spondilytis, multiple sclerosis, Wegener's granulomatosis, systemic lupus erythematosus, psoriasis and sarcoidosis.

The pharmaceutical formulations may conveniently be presented in unit dosage form and may be prepared by any of the methods well known in the art of pharmacy.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 2 µg and 150 µg of each therapeutically active ingredient. Alternatively, the active ingredient(s) may be presented without excipients.

Packaging of the formulation for inhalation may be carried out by using suitable inhaler devices such as the Novolizer SD2FL which is described in the following patent applications: WO 97/000703, WO 03/000325 and WO 03/061742.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

Effective doses are normally in the range of 2-2000 mg of active ingredient per day. Daily dosage may be administered in one or more treatments, preferably from 1 to 4 treatments, per day. Preferably, the active ingredients are administered once or twice a day.

When combinations of actives are used, it is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time.

Preferably, at least two, and more preferably all actives would be administered as an admixture.

The following preparations forms are cited as formulation examples:

Composition Example 1

50,000 capsules, each containing 100 mg 2-(3,5-difluoro-3'-methoxybiphenyl-4-ylamino)-5-methylnicotinic acid (active ingredient), were prepared according to the following formulation:

| Active ingredient | 5 Kg |
|---|---|
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets, each containing 50 mg of 2-(3,5-difluoro-3'-methoxybiphenyl-4-ylamino)-5-methylnicotinic acid (active ingredient), were prepared from the following formulation:

| Active ingredient | 2.5 Kg |
|---|---|
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:

1. A compound of formula (I),

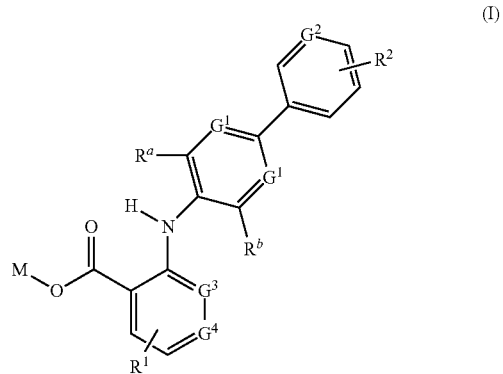

wherein
one of the $G^1$ groups is chosen from a nitrogen atom and a $CR^c$ group and the other $G^1$ group represents a $CR^c$ group;

$G^2$ represents a $CR^d$ group;

$R^1$ is chosen from hydrogen atoms, halogen atoms, $C_{1-4}$ alkyl groups, which may be optionally substituted by 1, 2 or 3 substituents chosen from halogen atoms and hydroxy groups, and $C_{3-8}$ cycloalkyl groups which may be optionally substituted by 1, 2 or 3 substituents chosen from halogen atoms and hydroxy groups;

$R^2$ is chosen from hydrogen atoms, halogen atoms, hydroxyl groups, $C_{1-4}$ alkyl groups, which may be optionally substituted by 1, 2 or 3 substituents chosen from halogen atoms and hydroxy groups, $C_{1-4}$ alkoxy groups, which may be optionally substituted by 1, 2 or 3 substituents chosen from halogen atoms and hydroxy groups, and $C_{3-8}$ cycloalkyl groups, which may be optionally substituted by 1, 2 or 3 substituents chosen from halogen atoms and hydroxy groups;

$R^a$, $R^b$ and $R^c$ are each independently chosen from hydrogen atoms, halogen atoms, $C_{1-4}$ alkyl groups, which may be optionally substituted by 1, 2 or 3 substituents chosen from halogen atoms and hydroxy groups, and $C_{1-4}$ alkoxy groups, which may be optionally substituted by 1, 2 or 3 substituents chosen from halogen atoms and hydroxy groups;

$R^d$ is chosen from hydroxy groups, $C_{1-3}$ alkoxy groups, 2,2,2-trifluoroethoxy groups and $C_{3-4}$cycloalkoxy groups;

one of the groups $G^3$ and $G^4$ is a nitrogen atom and the other is a CH group; and M is a hydrogen atom or an pharmaceutically acceptable cation;

with the proviso that, when at least one of the groups $R^a$ and $R^b$ represent a hydrogen atom, then $R^d$ is chosen from $C_{1-3}$ alkoxy groups, which may be optionally substituted by 1, 2 or 3 substituents chosen from halogen atoms and hydroxy groups, and $C_{3-4}$ cycloalkoxy groups, which may be optionally substituted by 1, 2 or 3 substituents chosen from halogen atoms and hydroxy groups;

or a pharmaceutically acceptable salt or N-oxide thereof.

2. The compound according to claim 1, wherein each of the $C_{1-4}$ alkyl groups, the $C_{3-8}$ cycloalkyl groups, the $C_{1-4}$ alkoxy groups and the $C_{3-8}$ cycloalkoxy groups is independently optionally substituted by 1, 2 or 3 halogen atoms.

3. The compound according to claim 1, wherein $R^1$ is chosen from hydrogen atoms, bromine atoms, fluorine atoms, methyl, ethyl, cyclopropyl and cyclobutyl groups.

4. The compound according to claim 1, wherein $G^3$ represents a nitrogen atom and $G^4$ represents a CH group.

5. The compound according to claim 1, wherein both $G^1$ groups represent a $CR^c$ group.

6. The compound according to claim 1, wherein each $R^c$ is independently chosen from hydrogen atoms, fluorine atoms, chlorine atoms and $C_{1-3}$ alkyl groups.

7. The compound according to claim 1, wherein $R^d$ is chosen from $C_{1-3}$ alkoxy groups, 2,2,2-trifluoroethoxy groups and $C_{3-4}$ cycloalkoxy groups.

8. The compound according to claim 1, wherein $R^a$ is chosen from fluorine atoms, methyl groups and trifluoromethoxy groups.

9. The compound according to claim 8, wherein $R^b$ is chosen from hydrogen atoms, fluorine atoms and chlorine atoms.

10. The compound according to claim 1, wherein $R^2$ is chosen from hydrogen atoms and halogen atoms.

11. The compound according to claim 10, wherein $R^2$ is chosen from hydrogen atoms and fluorine atoms.

12. A compound of formula (I),

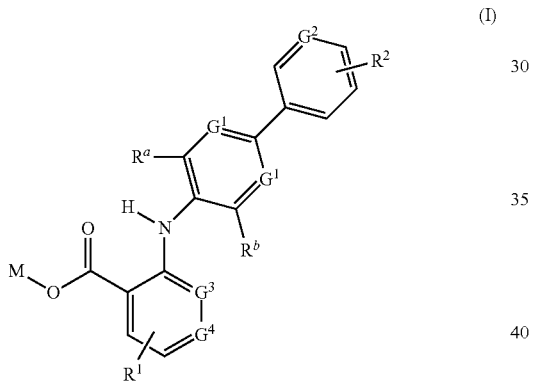

(I)

wherein
one of the $G^1$ groups is chosen from a nitrogen atom and a $CR^c$ group and the other $G^1$ group represents a $CR^c$ group;
$G^2$ is chosen from a nitrogen atom and a $CR^d$ group;
$R^1$ is chosen from hydrogen atoms, halogen atoms, $C_{1-4}$ alkyl groups, which may be optionally substituted by 1, 2 or 3 substituents chosen from halogen atoms and hydroxy groups, and $C_{3-8}$ cycloalkyl groups which may be optionally substituted by 1, 2 or 3 substituents chosen from halogen atoms and hydroxy groups;
$R^2$ is chosen from hydrogen atoms, halogen atoms, hydroxyl groups, $C_{1-4}$ alkyl groups, which may be optionally substituted by 1, 2 or 3 substituents chosen from halogen atoms and hydroxy groups, $C_{1-4}$ alkoxy groups, which may be optionally substituted by 1, 2 or 3 substituents chosen from halogen atoms and hydroxy groups, and $C_{3-8}$ cycloalkyl groups, which may be optionally substituted by 1, 2 or 3 substituents chosen from halogen atoms and hydroxy groups;
$R^a$, $R^b$ and $R^c$ are each independently chosen from hydrogen atoms, halogen atoms, $C_{1-4}$ alkyl groups, which may be optionally substituted by 1, 2 or 3 substituents chosen from halogen atoms and hydroxy groups, and $C_{1-4}$ alkoxy groups, which may be optionally substituted by 1, 2 or 3 substituents chosen from halogen atoms and hydroxy groups;
$R^d$ is chosen from hydrogen atoms, halogen atoms, hydroxyl groups, $C_{1-4}$ alkyl groups, which may be optionally substituted by 1, 2 or 3 substituents chosen from halogen atoms, and hydroxy groups, $C_{1-4}$ alkoxy groups, which may be optionally substituted by 1, 2 or 3 substituents chosen from halogen atoms and hydroxy groups, and $C_{3-8}$ cycloalkoxy groups, which may be optionally substituted by 1, 2 or 3 substituents chosen from halogen atoms and hydroxy groups;
$G^3$ represents a CH group and $G^4$ represents a nitrogen atom; and
M is a hydrogen atom or an pharmaceutically acceptable cation;
with the proviso that, when at least one of the groups $R^a$ and $R^b$ represent a hydrogen atom and $G^2$ is a $CR^d$ group, then $R^d$ is chosen from $C_{1-4}$ alkoxy groups, which may be optionally substituted by 1, 2 or 3 substituents chosen from halogen atoms and hydroxy groups, and $C_{3-8}$ cycloalkoxy groups, which may be optionally substituted by 1, 2 or 3 substituents chosen from halogen atoms and hydroxy groups;
or a pharmaceutically acceptable salt or N-oxide thereof.

13. A compound of formula (I),

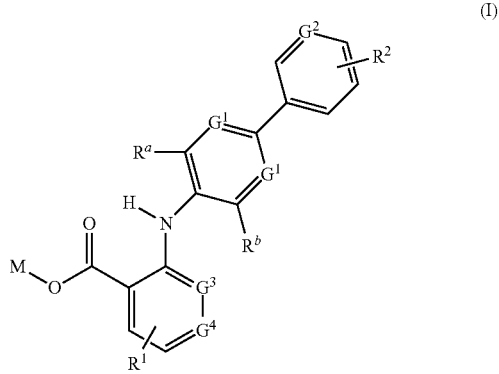

(I)

wherein
each $G^1$ group represents a $C(R^c)$ group, $R^a$ is a fluorine atom, $R^b$ is chosen from hydrogen atoms and fluorine atoms, $R^1$ is chosen from hydrogen atoms, bromine atoms, fluorine atoms, methyl, ethyl and cyclopropyl groups;
$G^2$ is chosen from C(OH), C(OMe) and C(OEt);
$R^2$ is chosen from hydrogen atoms, halogen atoms, hydroxyl groups, $C_{1-4}$ alkyl groups, which may be optionally substituted by 1, 2 or 3 substituents chosen from halogen atoms and hydroxy groups, $C_{1-4}$ alkoxy groups, which may be optionally substituted by 1, 2 or 3 substituents chosen from halogen atoms and hydroxy groups, and $C_{3-8}$ cycloalkyl groups, which may be optionally substituted by 1, 2 or 3 substituents chosen from halogen atoms and hydroxy groups;
$R^c$ is chosen from hydrogen atoms, halogen atoms, $C_{1-4}$ alkyl groups, which may be optionally substituted by 1, 2 or 3 substituents chosen from halogen atoms and hydroxy groups, and $C_{1-4}$ alkoxy groups, which may be optionally substituted by 1, 2 or 3 substituents chosen from halogen atoms and hydroxy groups;

$R^d$ is chosen from hydrogen atoms, halogen atoms, hydroxyl groups, $C_{1-4}$ alkyl groups, which may be optionally substituted by 1, 2 or 3 substituents chosen from halogen atoms, and hydroxy groups, $C_{1-4}$ alkoxy groups, which may be optionally substituted by 1, 2 or 3 substituents chosen from halogen atoms and hydroxy groups, and $C_{3-8}$ cycloalkoxy groups, which may be optionally substituted by 1, 2 or 3 substituents chosen from halogen atoms and hydroxy groups;

one of the groups $G^3$ and $G^4$ is a nitrogen atom and the other is a CH group; and M is a hydrogen atom or an pharmaceutically acceptable cation;

with the proviso that, when $R^b$ represents a hydrogen atom, then $R^d$ is chosen from $C_{1-4}$ alkoxy groups, which may be optionally substituted by 1, 2 or 3 substituents chosen from halogen atoms and hydroxy groups, and $C_{3-8}$ cycloalkoxy groups, which may be optionally substituted by 1, 2 or 3 substituents chosen from halogen atoms and hydroxy groups;

or a pharmaceutically acceptable salt or N-oxide thereof.

14. The compound according to claim 13, wherein each $G^1$ group represents a CH group and $G^2$ is chosen from C(OMe) and C(OEt).

15. The compound according to claim 13, wherein $R^c$ is a hydrogen atom, $R^d$ is chosen from $C_{1-3}$ alkoxy groups and $C_{3-4}$ cycloalkoxy groups, and $R^2$ is a hydrogen atom.

16. The compound according to claim 13, wherein $R^d$ is chosen from a hydroxy group and $C_{1-3}$ alkoxy groups.

17. The compound according to claim 15, wherein $R^d$ is a $C_{1-3}$ alkoxy group.

18. The compound according to claim 15, wherein $G^3$ represents a nitrogen atom, $G^4$ represents a CH group, and $R^b$ is a fluorine atom.

19. The compound according to claim 15, wherein $G^3$ represents a CH group, and $G^4$ represents a nitrogen atom.

20. A compound chosen from:
2-(3-Fluoro-3'-methoxybiphenyl-4-ylamino)nicotinic acid;
2-(3'-Ethoxy-3-fluorobiphenyl-4-ylamino)nicotinic acid;
2-(3'-Ethoxy-3-(trifluoromethoxy)biphenyl-4-ylamino) nicotinic acid;
2-(3'-Methoxy-3-(trifluoromethoxy)biphenyl-4-ylamino) nicotinic acid;
2-(2,5-Difluoro-3'-methoxybiphenyl-4-ylamino)nicotinic acid;
2-(3'-Ethoxy-2,5-difluorobiphenyl-4-ylamino) nicotinic acid;
2-(2',3-difluoro-3'-methoxybiphenyl-4-ylamino)nicotinic acid;
2-(3-Chloro-3'-ethoxybiphenyl-4-ylamino)nicotinic acid;
2-(3-Chloro-3'-methoxybiphenyl-4-ylamino)nicotinic acid;
2-(3'-Cyclobutoxy-3-fluorobiphenyl-4-ylamino)nicotinic acid;
2-(3-Fluoro-3'-(2,2,2-trifluoroethoxy)biphenyl-4-ylamino)nicotinic acid;
2-(3'-Cyclobutoxy-3,5-difluorobiphenyl-4-ylamino)nicotinic acid;
2-(3'-Ethoxy-3,5-difluorobiphenyl-4-ylamino)nicotinic acid;
2-(3,5-Difluoro-3'-methoxybiphenyl-4-ylamino)nicotinic acid;
Lithium 3-(3'-ethoxy-3-fluorobiphenyl-4-ylamino) isonicotinate;
Lithium 3-(3-fluoro-3'-methoxybiphenyl-4-ylamino) isonicotinate;
Lithium 3-(3'-methoxy-3-(trifluoromethoxy)biphenyl-4-ylamino)isonicotinate;
Lithium 3-(3-fluoro-3'-(trifluoromethoxy)biphenyl-4-ylamino)isonicotinate;
2-(3'-Ethoxybiphenyl-4-ylamino)nicotinic acid;
2-(2',3-Difluoro-5'-isopropoxybiphenyl-4-ylamino)nicotinic acid;
2-(3-Fluoro-3'-methoxybiphenyl-4-ylamino)-5-methylnicotinic acid;
2-(3,5-Difluoro-3'-hydroxybiphenyl-4-ylamino)nicotinic acid;
5-Bromo-2-(3-fluoro-3'-methoxybiphenyl-4-ylamino) nicotinic acid;
5-Bromo-2-(3,5-difluoro-3'-methoxybiphenyl-4-ylamino)nicotinic acid;
5-Cyclopropyl-2-(3-fluoro-3'-methoxybiphenyl-4-ylamino)nicotinic acid;
2-(3,5-Difluoro-3'-methoxybiphenyl-4-ylamino)-5-methylnicotinic acid;
2-(3'-Ethoxy-5-fluoro-2-methylbiphenyl-4-ylamino)nicotinic acid;
2-(5-Fluoro-3'-methoxy-2-methylbiphenyl-4-ylamino) nicotinic acid;
2-(3'-ethoxy-3,5-difluorobiphenyl-4-ylamino)-5-methylnicotinic acid;
5-cyclopropyl-2-(3'-ethoxy-3,5-difluorobiphenyl-4-ylamino)nicotinic acid;
2-(3,5-difluoro-3'-methoxybiphenyl-4-ylamino)-5-ethylnicotinic acid;
5-bromo-2-(3'-ethoxy-2,5-difluorobiphenyl-4-ylamino) nicotinic acid;
5-cyclopropyl-2-(3'-ethoxy-2,5-difluorobiphenyl-4-ylamino)nicotinic acid;
2-(5-fluoro-3'-methoxy-2-methylbiphenyl-4-ylamino)-5-methylnicotinic acid;
5-cyclopropyl-2-(5-fluoro-3'-methoxy-2-methylbiphenyl-4-ylamino)nicotinic acid;
2-(2',3,5-trifluoro-3'-methoxybiphenyl-4-ylamino)nicotinic acid;
2-(3'-cyclopropoxy-3,5-difluorobiphenyl-4-ylamino) nicotinic acid;
5-cyclopropyl-2-(2,5-difluoro-3'-methoxybiphenyl-4-ylamino)nicotinic acid;
2-(3'-cyclopropoxy-3,5-difluorobiphenyl-4-ylamino)-5-cyclopropylnicotinic acid;
5-chloro-2-(3,5-difluoro-3'-methoxybiphenyl-4-ylamino) nicotinic acid;
2-(2,3,5-trifluoro-3'-methoxybiphenyl-4-ylamino)nicotinic acid;
2-(3,5-difluoro-3'-methoxy-2-methylbiphenyl-4-ylamino)nicotinic acid;
2-(3,5-difluoro-2-methyl-3'-(trifluoromethoxy)biphenyl-4-ylamino)nicotinic acid;
2-(2,3,5,6-tetrafluoro-3'-methoxybiphenyl-4-ylamino) nicotinic acid;
3-(3'-cyclopropoxy-3-fluorobiphenyl-4-ylamino)isonicotinic acid; or a pharmaceutically acceptable salt or a N-oxide thereof.

21. A method of treating a pathological condition or disease, comprising administering to a mammal in need thereof, an effective amount of a compound according to claim 1, wherein the pathological condition or disease is chosen from rheumatoid arthritis, psoriatic arthritis, and multiple sclerosis.

22. A method of treating a pathological condition or disease, comprising administering to a mammal in need thereof an effective amount of a compound according to claim 1, wherein the pathological condition or disease is chosen from ankylosing spondylitis, Wegener's granulomatosis, systemic lupus erythematosus, psoriasis and sarcoidosis.

23. A composition comprising (i) a compound according to claim 1; and (ii) another compound chosen from:
 a) Anti-TNF-alpha monoclonal antibodies;
 b) TNF-alpha Antagonists;
 c) Calcineurin (PP-2B) Inhibitors / INS Expression Inhibitors;
 d) IL-1 Receptor Antagonists;
 e) Anti-CD20 monoclonal antibodies;
 f) p38 Inhibitors;
 g) NF-kappaB (NFKB) Activation Inhibitors; and
 h) Dihydrofolate Reductase (DHFR) Inhibitors.

24. The composition according to claim 23, wherein:
 a) the Anti-TNF-alpha monoclonal antibody is chosen from Infliximab, Certolizumab pegol, Golimumab, Adalimumab and AME-527;
 b) the TNF-alpha Antagonist is chosen from Etanercept, Lenercept, Onercept and Pegsunercept;
 c) the Calcineurin (PP-2B) Inhibitor / INS Expression Inhibitor is chosen from cyclosporine A, Tacrolimus and ISA-247;
 d) the IL-1 Receptor Antagonist is chosen from Anakinra and AMG-719;
 e) the Anti-CD20 monoclonal antibody is chosen from Rituximab, Ofatumumab, Ocrelizumab and TRU-015;
 f) the p38 Inhibitor is chosen from AMG-548, ARRY-797, Chlormethiazole edisylate, Doramapimod, PS-540446, SB-203580, SB-242235, SB-235699, SB-281832, SB-681323, SB-856553, KC-706, LEO-1606, LEO-15520, SC-80036, SD-06, RWJ-67657, RO-3201195, RO-4402257, AVE-9940, SCIO-323, SCIO-469, TA-5493, and VX-745 and VX-702;
 g) the NF-kappaB (NFKB) Activation Inhibitor is chosen from Sulfasalazine and Iguratimod; and the Dihydrofolate Reductase (DHFR) Inhibitor is chosen from Methrotexate, Aminopterin and CH-1504.

25. The compound according to claim 20, chosen from
2-(3'-Ethoxy-3-(trifluoromethoxy)biphenyl-4-ylamino) nicotinic acid;
2-(3,5-Difluoro-3'-methoxybiphenyl-4-ylamino)nicotinic acid;
2-(3'-cyclopropoxy-3,5-difluorobiphenyl-4-ylamino)-5-cyclopropylnicotinic acid;
2-(2,3,5-trifluoro-3'-methoxybiphenyl-4-ylamino)nicotinic acid;
2-(3,5-difluoro-2-methyl-3'-(trifluoromethoxy)biphenyl-4-ylamino)nicotinic acid;
2-(2,3,5,6-tetrafluoro-3'-methoxybiphenyl-4-ylamino) nicotinic acid;
or a pharmaceutically acceptable salt or a N-oxide thereof.

26. The compound according to claim 20, wherein the compound is 2-(3,5-Difluoro-3'-methoxybiphenyl-4-ylamino)nicotinic acid or a pharmaceutically acceptable salt or a N-oxide thereof.

* * * * *

UNITED STATES PATENT AND TRADEMARK OFFICE
CERTIFICATE OF CORRECTION

PATENT NO. : 8,258,308 B2
APPLICATION NO. : 12/520237
DATED : September 4, 2012
INVENTOR(S) : Julio Cesar Castro Palomino Laria et al.

Page 1 of 1

It is certified that error appears in the above-identified patent and that said Letters Patent is hereby corrected as shown below:

Title page, item (73), after "Assignee:",
"Laboratorios Almirall, S.A." should read -- Almirall, S.A. --.

Signed and Sealed this
Twelfth Day of February, 2013

Teresa Stanek Rea
*Acting Director of the United States Patent and Trademark Office*